US009745347B2

(12) United States Patent
Bar-Shavit

(10) Patent No.: US 9,745,347 B2
(45) Date of Patent: Aug. 29, 2017

(54) PAR1 AND PAR2 C-TAIL PEPTIDES AND PEPTIDE MIMETICS

(75) Inventor: Rachel Bar-Shavit, Shoresh (IL)

(73) Assignee: Hadasit Medical Research Services and Development Ltd., Jerusalem (IL)

(*) Notice: Subject to any disclaimer, the term of this patent is extended or adjusted under 35 U.S.C. 154(b) by 0 days.

(21) Appl. No.: 13/977,545

(22) PCT Filed: Dec. 29, 2011

(86) PCT No.: PCT/IL2011/050083
§ 371 (c)(1),
(2), (4) Date: Jun. 28, 2013

(87) PCT Pub. No.: WO2012/090207
PCT Pub. Date: Jul. 5, 2012

(65) Prior Publication Data
US 2013/0331333 A1 Dec. 12, 2013

Related U.S. Application Data

(60) Provisional application No. 61/428,290, filed on Dec. 30, 2010.

(51) Int. Cl.
| | | |
|---|---|---|
| *A61K 38/10* | (2006.01) | |
| *C07K 7/08* | (2006.01) | |
| *A61K 38/08* | (2006.01) | |
| *C07K 14/705* | (2006.01) | |
| *C07K 14/72* | (2006.01) | |
| *C07K 7/06* | (2006.01) | |
| *A61K 38/17* | (2006.01) | |

(52) U.S. Cl.
CPC .......... *C07K 7/08* (2013.01); *A61K 38/08* (2013.01); *A61K 38/10* (2013.01); *C07K 7/06* (2013.01); *C07K 14/705* (2013.01); *C07K 14/723* (2013.01); *A61K 38/177* (2013.01)

(58) Field of Classification Search
None
See application file for complete search history.

(56) References Cited

U.S. PATENT DOCUMENTS

| 2007/0053911 A1* | 3/2007 | Golz et al. | 424/146.1 |
| 2007/0196865 A1* | 8/2007 | Cowan | 435/7.2 |

FOREIGN PATENT DOCUMENTS

| EP | 2 267 125 | 12/2010 |
| WO | WO-00/63371 | 10/2000 |
| WO | WO-01/00656 | 1/2001 |
| WO | WO-2004/002418 | 1/2004 |
| WO | WO-2004/003202 | 1/2004 |
| WO | WO-2004/080373 | 9/2004 |
| WO | WO-2005/029035 | 3/2005 |
| WO | WO-2007/075808 | 7/2007 |
| WO | WO-2010/118435 | 10/2010 |

OTHER PUBLICATIONS

Barry et al, J Med Chem, 2010; 53:7428-7440.*
Grisaru-Granovsky et al, Reproductive Sciences, Mar. 2010; 17(3) Supp 1:121A.*
Johnson and Tracey, 'Peptide and Protein Drug Delivery', In: Encyclopedia of Controlled Drug Delivery, vol. 2, 1999, pp. 816-833.*
Brown, 2005, Expert Opinion Drug Delivery, vol. 2(1), pp. 29-42.*
Mahmood et al, Clin Pharmacokinet, 2005, 44:331-347.*
Agarwal, A. et al. (Sep. 2008). "Targeting a Metalloprotease-PAR1 Signaling System with Cell-Penetrating Pepducins Inhibits Angiogenesis, Ascites, and Progression of Ovarian Cancer," *Molecular Cancer Therapeutics* 7(9):2746-2757.
Barry, G. D. et al. (2010). "Novel Agonists and Antagonists for Human Protease Activated Receptor 2," *Journal of Medicinal Chemistry* 53(20):7428-7440.
Booden, M. A. et al. (Mar. 2004). "Persistent Signaling by Dysregulated Thrombin Receptor Trafficking Promotes Breast Carcinoma Cell Invasion," *Molecular and Cellular Biology* 24(5):1990-1999.
Chen, R. et al. (May 2001). "Regulation of PH-domain-containing Tyrosine Kinase Etk by Focal Adhesion Kinase Through the FERM Domain," *Nature Cell Biology* 3:439-444.
Cohen, I. et al. (Jun. 2010). "Etk/Bmx Regulates Proteinase-Activated-Receptor1 ($PAR_1$) in Breast Cancer Invasion: Signaling Partners, Hierarchy and Physiological Significance," *PLoS One* 5(6):1-15.
Connolly, A. J. et al. (Jun. 1996). "Role of the Thrombin Receptor in Development and Evidence for a Second Receptor," *Nature* 381:516-519.
Desgrosellier, J. S. et al. (Oct. 2009). "An Integrin $\alpha_v\beta_3$-c-Src Oncogenic Unit Promotes Anchorage-independence and Tumor Progression," *Nature Medicine* 15(10):1163-1170.
Even-Ram, S. et al. (Aug. 1998). "Thrombin Receptor Overexpression in Malignant and Physiological Invasion Processes," *Nature Medicine* 4(8):909-914.
Granovsky-Grisaru, S. et al. (Jul. 2006). "The Pattern of Protease Activated Receptor 1 (PAR1) Expression in Endometrial Carcinoma," *Gynecologic Oncology* 103:802-806.
Griffin, C. T. et al. (Aug. 2001). "A Role for Thrombin Receptor Signaling in Endothelial Cells During Embryonic Development," *Science* 293:1666-1670.
Grisaru-Granovsky, S. et al. (2005). "Differential Expression of Protease Activated Recepter 1 (Par1) and pY397FAK in Benign and Malignant Human Ovarian Tissue Samples," *International Journal of Cancer* 113:372-378.
Groeger, A. M. et al. (2004). "Prognostic Value of Immunohistochemical Expression of p53, bax, Bcl-2 and $Bcl-x_L$ in Resected Non-small-cell Lung Cancers," *Histopathology* 44:54-63.
Hammes, S. R. et al. (Feb. 1999). "Protease-Activated Receptor-1 Can Mediate Responses to SFLLRN in Thrombin-Desensitized Cells: Evidence for a Novel Mechanism for Preventing or Terminating Signaling by PAR1's Tethered Ligand," *Biochemistry* 38:2486-2493.

(Continued)

*Primary Examiner* — Mark Halvorson
(74) *Attorney, Agent, or Firm* — Morrison & Foerster LLP

(57) ABSTRACT

The present invention concerns isolated PAR1 cytoplasmic tail (c-tail) peptides and isolated PAR2 cytoplasmic tail (c-tail) peptides, as well as compositions comprising these peptides, uses thereof and methods of treating various diseases, in particular cancer.

3 Claims, 22 Drawing Sheets

(56) References Cited

OTHER PUBLICATIONS

Iwaki, K. et al. (2008). A Small Interfering RNA Targeting Proteinase-Activated Receptor-2 is Effective in Suppression of Tumor Growth in a Panc1 Xenograft Model, *International Journal of Cancer* 122:658-663.

Jining, L. et al. (2004). "Design, Structure and Biological Activity of β-turn Peptides of CD2 Protein for Inhibition of T-cell Adhesion," *European Journal of Biochemistry* 271:2873-2886.

Kuruppu, D. et al. (Jan. 2002). "Changes in the Microvascular Architecture of Colorectal Liver Metastases Following the Administration of SMANCS/Lipiodol," *Journal of Surgical Research* 103(1):47-54.

Nierodzik, M. L. et al. (Nov. 1998). "Protease-Activated Receptor 1 (PAR-1) is Required and Rate-Limiting for Thrombin-Enhanced Experimental Pulmonary Metastasis," *Blood* 92(10):3694-3700.

Pelicci, G. et al. (Jul. 1992). "A Novel Transforming Protein (SHC) with an SH2 Domain is Implicated in Mitogenic Signal Transduction," *Cell* 70:93-104.

Pronk, G. J. et al. (Mar. 1993). "Insulin-induced Phosphorylation of the 46- and 52-kDa Shc Proteins," *The Journal of Biological Chemistry* 268(8):5748-5753.

Qiu, Y. et al. (Mar. 1998). "Etk/Bmx, a Tyrosine Kinase with a Pleckstrin-homology Domain, is an Effector of Phosphatidylinositol 3'-kinase and is Involved in Interleukin 6-induced Neuroendocrine Differentiation of Prostate Cancer Cells," *Proceedings of the National Academy of Sciences* 95:3644-3649.

Rebecchi, M. J. et al. (1998). "Pleckstrin Homology Domains: A Common Fold with Diverse Functions," *Annual Review of Biophysics and Biomolecular Structure* 27:503-528.

Salah, Z. et al. (Jan. 2005). "Identification of a Novel Functional Androgen Response Element Within hPar1 promoter: Implications to Prostate Cancer Progression," *The FASEB Journal* 19:62-72.

Shapiro, M. J. et al. (Dec. 1996). "Role of the Thrombin Receptor's Cytoplasmic Tail in Intracellular Trafficking," *The Journal of Biological Chemistry* 271(51):32874-32880.

Su, S. et al. (2009). "Proteinase-activated Receptor 2 Expression in Breast Cancer and its Role in Breast Cancer Cell Migration," *Oncogene* 28:3047-3057.

Tsai, Y-T. et al. (Mar. 2000). "Etk, a Btk Family Tyrosine Kinase, Mediates Cellular Transformation by Linking Src to STAT3 Activation," *Molecular and Cellular Biology* 20(6):2043-2054.

International Search Report dated Jul. 16, 2012, directed to International Application No. PCT/IL2011/050083; 4 pages.

Jaber, M. et al. (2014). "Protease-activated-receptor-2 affects protease-activated-receptor-1-driven breast cancer," *Cell. Mol. Life. Sci.* 71:2517-2533.

\* cited by examiner

1A

| Ezrin | | GRB7 | | PI3K p85 | |
|---|---|---|---|---|---|
| | Btk | | p 130CAS | | VECAM-1 |
| E-cadherin | | ICAM-1 | | Rho A | |
| | FAK | | p 38MAPK | | Yes |
| Catenin-β | | Integrin αv | | p21 WAF1 | |
| | Flt-3/2 | | SHC | | Syk |
| Csk | | Integrin β 3 | | Src | |
| | Fyn | | Paxillin | | Jun-B |
| Erk-1 | | JNK-1,2,3 | | Sos1/2 | |
| | GRB2 | | PLC γ | | Erk-2 |

1B

Fig. 2
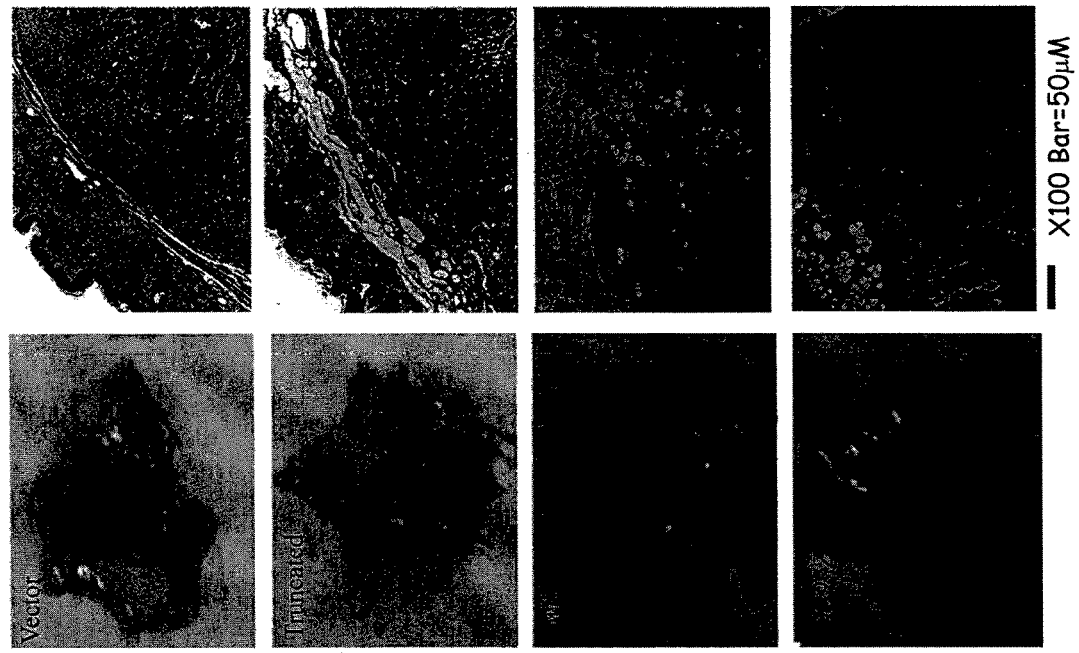
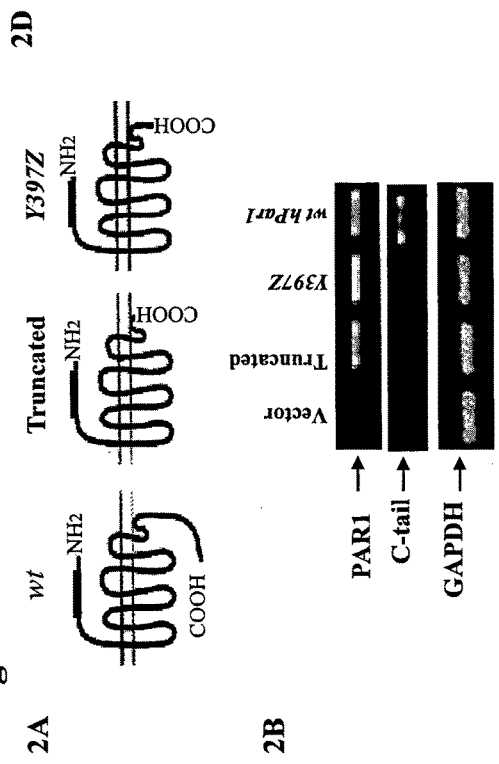
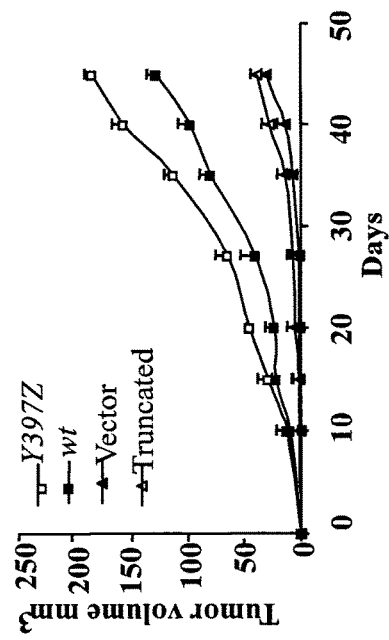

Fig. 3
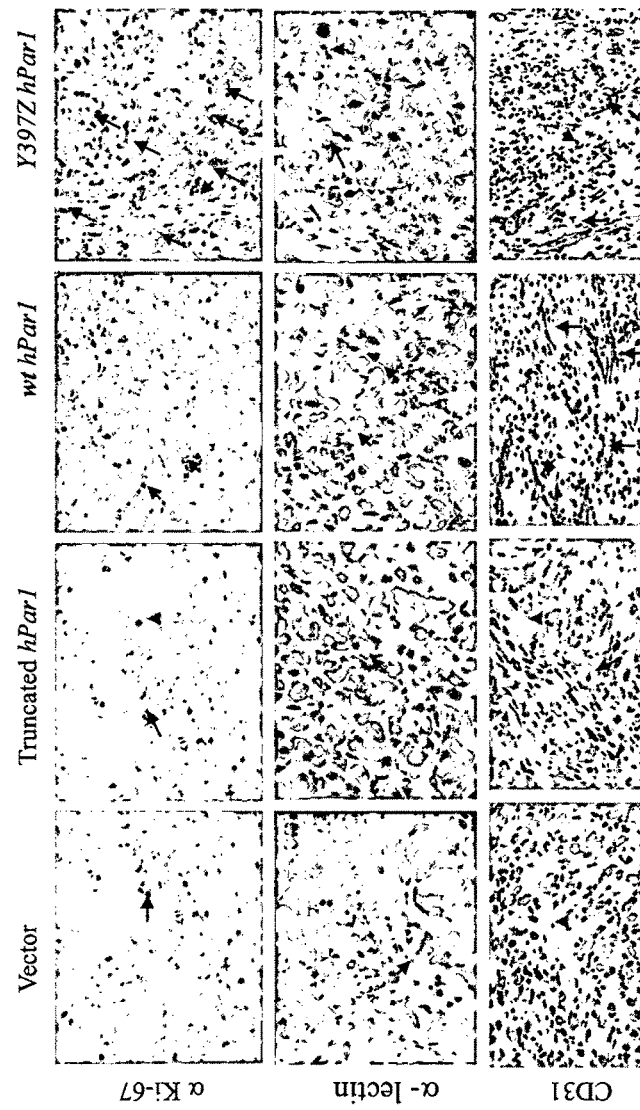
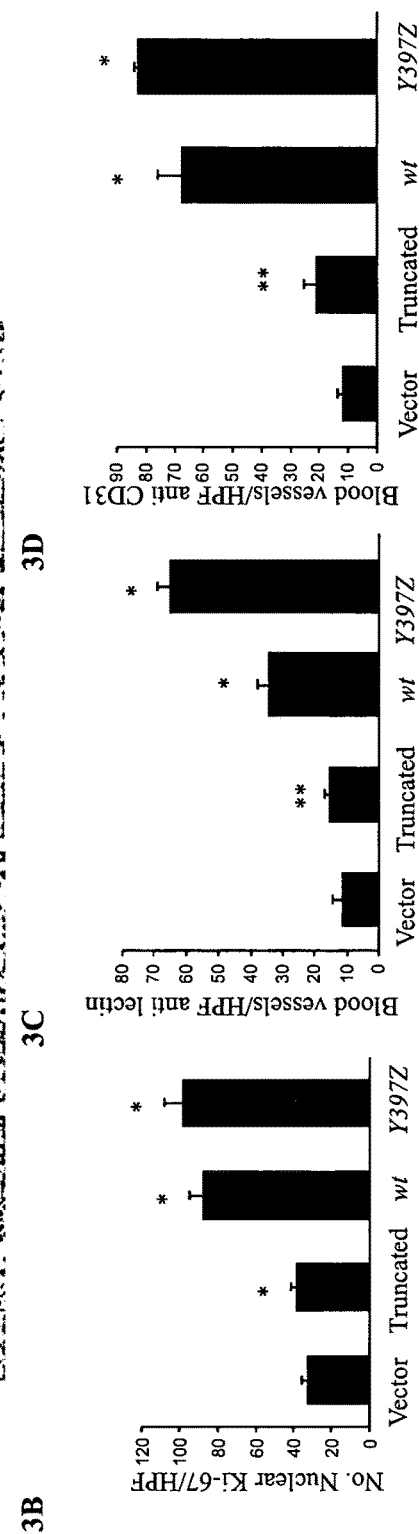

US 9,745,347 B2

PAR1 AND PAR2 C-TAIL PEPTIDES AND PEPTIDE MIMETICS

REFERENCE TO RELATED APPLICATIONS

This application is a national stage application under 35 USC 371 of International Application No. PCT/IL2011/050083, filed Dec. 29, 2011, which claims the priority of Provisional Application No. 61/428,290, filed Dec. 30, 2010, the entire contents of which are incorporated herein by reference.

FIELD OF THE INVENTION

This invention relates to compositions and methods for treating various pathologies, in particular cancer, wherein the compositions comprise peptides and peptide mimetics which inhibit PAR signal transduction.

INCORPORATION BY REFERENCE

The content of the following submission on ASCII text file is incorporated herein by reference in its entirety: a computer readable form (CRF) of the Sequence Listing (file name: 266722000800SEQLIST.txt, date recorded: Aug. 25, 2015, size: 14 KB).

BACKGROUND OF THE INVENTION

The family of mammalian protease-activated receptors (PARs), belonging to G protein-coupled receptor (GPCR) is composed of four genes. PAR1 is activated following the release of N-terminal peptide and the exposure of an otherwise hindered ligand. This exclusive mode of activation serves as a general paradigm for the entire PAR family. Expression of hPar1 and epithelial tumor progression are directly correlated in both clinically obtained biopsy specimens and a wide spectrum of differentially metastatic cell lines (Even-Ram S, et al. (1998) *Nat Med* 4: 909-914). PAR1 has been shown to play a central role in the invasive and metastatic cancers of breast, ovaries, lung, colon, prostate and melanoma (Grisaru-Granovsky S, et al. (2005) *Int J Cancer* 113: 372-378; Nierodzik M L, et al (1998) *Blood* 92(10):3694-700; Salah Z, et al (2005) *FASEB J* 19(1):62-72; Granovsky-Grisaru S, et al (2006) *Gynecol Oncol* 103(3):802-6; Agarwal A, et al (2008) *Mol Cancer Ther* 7(9): 2746-57).

Importantly, PAR1 cellular trafficking and signal termination appear to occur in a different mode than other GPCRs. Instead of recycling back to the cell surface after ligand stimulation, activated PAR1 is sorted to the lysosomes and degraded. Aberrant PAR1 trafficking, resulting in receptor-populated cell surfaces and causing prolonged and persistent signals, has been found in breast cancer (Booden M A, et al (2004) *Mol Cell Biol.* 24:1990-1999). While cellular trafficking of PAR1 impinges on the extent and mode of signaling, identification of individual PAR1 signaling partners and their contribution to breast cancer progression remain yet to be elucidated.

Surprisingly, PAR2, the second member which is not considered a thrombin-receptor (in contrast to PAR1, 3 and 4) was found to be connected to coagulation by virtue of its activation by other coagulation proteases such as tissue factor; TF bound to FVIIa (factor VIIa); TF-FVIIa. PAR2 was associated with promotion of breast cancer (Su S, et al (2009) *Oncogene* 28(34):3047-57).

SUMMARY OF THE INVENTION

The present invention is based on the identification of a binding interaction between a cytoplasmic portion of PAR1 or PAR2 and PH-domain containing proteins.

As a non-limiting example, a binding interaction was identified between the cytoplasmic portion of PAR1 or PAR2 and the PH-domain containing proteins Etk/Bmx, Akt and Vav3. Specifically, a PAR1 cytoplasmic-tail (c-tail) peptide was shown to penetrate into cells in culture and to interfere in the binding reaction between PAR1 and Etk/Bmx.

Moreover, abrogation of the binding interaction between PAR1 and the PH-domain containing protein Etk/Bmx resulted in reduction in PAR1 induced oncogenic activity.

Accordingly, by a first of its aspects, the present invention provides an isolated PAR1 cytoplasmic tail (c-tail) peptide selected from the group consisting of:
- (a) an isolated PAR1 c-tail peptide capable of interfering in the binding reaction between PAR1 and a PH-domain containing protein;
- (b) an isolated PAR1 c-tail peptide comprising SEQ ID NO: 1;
- (c) an isolated PAR1 c-tail peptide consisting of the sequence SSECQRYVYSIL (SEQ ID NO: 3);
- (d) an isolated PAR1 c-tail peptide consisting of the sequence SSECQRYVYSILCCK (SEQ ID NO: 4); and
- (e) any fragment or modification of the peptides of (a) (b) (c) or (d).

In certain embodiments the PH-domain containing protein is selected from the group consisting of Etk/Bmx, Akt and Vav3. In a specific embodiment, the PH-domain containing protein is Etk/Bmx.

In another aspect, the present invention provides an isolated PAR2 c-tail peptide selected from the group consisting of:
- (a) an isolated PAR2 c-tail peptide capable of interfering in the binding reaction between PAR2 and a PH-domain containing protein;
- (b) an isolated PAR2 c-tail peptide comprising SEQ ID NO: 2; and
- (c) any fragment or modification of the peptides of (a) or (b).

In another aspect, the present invention provides a method of inhibiting PAR1 mediated signal transduction comprising administering an agent capable of selectively inhibiting the binding of PAR1 and a PH-domain containing protein, in particular Etk/Bmx.

In another aspect, the present invention provides a method of treating a disease comprising administering a therapeutically effective amount of an agent capable of selectively inhibiting the binding of PAR1 and a PH-domain containing protein, in particular Etk/Bmx, or a pharmaceutical composition comprising said agent to a patient in need thereof.

In certain embodiments said agent is a peptide.

In another aspect, the present invention provides a method of treating a disease comprising administering a therapeutically effective amount of a peptide, or a pharmaceutical composition comprising the peptide to a patient in need thereof, wherein the peptide is selected from the group consisting of:
- (a) An isolated PAR1 c-tail peptide comprising the amino acid sequence CQRYVYS (SEQ ID NO: 1);
- (b) an isolated PAR1 c-tail peptide consisting of the sequence SSECQRYVYSIL (SEQ ID NO: 3);

(c) An isolated PAR1 c-tail peptide consisting of the amino acid sequence SSECQRYVYSILCCK (SEQ ID NO: 4); and
(d) any fragment or modification of the peptides of (a) (b) or (c).

In certain embodiments, the method further comprises administering an additional therapeutic agent.

In another aspect, the present invention provides a method of inhibiting PAR2 mediated signal transduction comprising administering an agent capable of selectively inhibiting the binding of PAR2 and a PH-domain containing protein, in particular Etk/Bmx.

In another aspect, the present invention provides a method of treating a disease comprising administering a therapeutically effective amount of an agent capable of selectively inhibiting the binding of PAR2 and a PH-domain containing protein, in particular Etk/Bmx, or a pharmaceutical composition comprising said agent to a patient in need thereof.

In certain embodiments said agent is a peptide.

In another aspect, the present invention provides a method of treating a disease comprising administering a therapeutically effective amount of a peptide, or a pharmaceutical composition comprising the peptide to a patient in need thereof, wherein the peptide is selected from the group consisting of:
(a) An isolated PAR2 c-tail peptide comprising the amino acid sequence SHDFRDHA (SEQ ID NO: 2); and
(b) any fragment or modification of the peptide of (a).

In certain embodiments, the method further comprises administering an additional therapeutic agent.

In accordance with certain embodiments, said disease is cancer.

In certain embodiments said cancer is selected from the group consisting of breast cancer, ovary cancer, lung cancer, colon cancer, prostate cancer and melanoma.

In another aspect, the present invention provides a pharmaceutical composition comprising a peptide of the invention together with a pharmaceutically acceptable carrier or diluent.

In a specific embodiment, the present invention provides a pharmaceutical composition comprising a peptide of the invention together with a pharmaceutically acceptable carrier or diluent for the treatment of cancer.

The invention also encompasses a pharmaceutical composition comprising a combination of at least one isolated PAR1 c-tail peptide selected from the group consisting of:
(a) an isolated PAR1 c-tail peptide capable of interfering in the binding reaction between PAR1 and a PH-domain containing protein;
(b) an isolated PAR1 c-tail peptide comprising SEQ ID NO: 1;
(c) an isolated PAR1 c-tail peptide consisting of the sequence SSECQRYVYSIL (SEQ ID NO: 3);
(d) an isolated PAR1 c-tail peptide consisting of the sequence SSECQRYVYSILCCK (SEQ ID NO: 4); and
(e) any fragment or modification of the peptides of (a) (b) (c) or (d).
and at least one isolated PAR2 c-tail peptide selected from the group consisting of:
(a) an isolated PAR2 c-tail peptide capable of interfering in the binding reaction between PAR2 and a PH-domain containing protein;
(b) an isolated PAR2 c-tail peptide comprising SEQ ID NO: 2; and
(c) any fragment or modification of the peptides of (a) or (b).

In a specific embodiment, the invention encompasses a pharmaceutical composition comprising a combination of at least one isolated peptide comprising SEQ ID NO: 1 or any fragment or modification thereof, and at least one isolated peptide comprising SEQ ID NO: 2 or any fragment or modification thereof.

In a specific embodiment the pharmaceutical compositions of the invention are for the treatment of cancer. In yet other embodiments the pharmaceutical compositions further comprise an additional therapeutic agent.

The invention also concerns a peptide according to the above or a pharmaceutical composition according to the above for use in combination with another therapeutic agent.

In another aspect the invention concerns an isolated peptide comprising an amino acid sequence of the PAR1 cytoplasmic-tail for use as a medicament.

In yet another aspect the invention concerns an isolated peptide comprising an amino acid sequence of the PAR2 cytoplasmic-tail for use as a medicament.

In another aspect, the present invention provides use of an agent capable of selectively inhibiting the binding of PAR1 and a PH-domain containing protein, in the preparation of a pharmaceutical composition for treating a disease.

In one embodiment, said disease is cancer.

In another embodiment, said agent is a peptide.

In yet another aspect, the present invention provides use of a peptide in the preparation of a pharmaceutical composition for treating a disease, wherein the peptide is selected from the group consisting of:
(a) An isolated PAR1 c-tail peptide comprising the amino acid sequence CQRYVYS (SEQ ID NO: 1);
(b) an isolated PAR1 c-tail peptide consisting of the sequence SSECQRYVYSIL (SEQ ID NO: 3);
(c) An isolated PAR1 c-tail peptide consisting of the amino acid sequence SSECQRYVYSILCCK (SEQ ID NO: 4); and
(d) any fragment or modification of the peptides of (a) (b) or (c).

In one embodiment, the use further comprises administering an additional therapeutic agent.

In yet another aspect, the present invention provides use of an agent capable of selectively inhibiting the binding of PAR2 and a PH-domain containing protein, in the preparation of a pharmaceutical composition for treating a disease.

In one embodiment said disease is cancer.

In another embodiment said agent is a peptide.

In another aspect, the present invention provides use of a peptide in the preparation of a pharmaceutical composition for the treatment of a disease, wherein the peptide is selected from the group consisting of:
(a) An isolated PAR2 c-tail peptide comprising the amino acid sequence SHDFRDHA (SEQ ID NO: 2); and
(b) any fragment or modification of the peptide of (a).

In one embodiment, the use further comprises administering an additional therapeutic agent.

BRIEF DESCRIPTION OF THE DRAWINGS

In order to understand the invention and to see how it may be carried out in practice, embodiments will now be described, by way of non-limiting example only, with reference to the accompanying drawings, in which:

FIG. 2A is a schematic representation of the structure of various hPAR1 constructs: wild-type hPar1 (wt), a truncated form (Truncated) representing the mutant hPar1 L369Z which lacks the entire cytoplasmic tail, and Y397Z, another hPar1 deletion mutant which exhibits persistent signaling due to impaired internalization. FIG. 2B demonstrates semi-quantitative RT-PCR analysis of cells transfected with various hPar1 constructs (wt-hPar1, Truncated, Y397Z, and control (empty vector)). Upper panel: $PAR_1$ N-terminus, middle panel: C-terminus. All the tested cells expressed similar GAPDH levels. FIG. 2C is a graph demonstrating mouse mammary tumor growth in animals implanted with cells expressing wt hPar1 and variants. The graph demonstrates increase in tumor volume ($mm^3$, mean±SD) with time, for each of the tested groups: wt hPar1 (■), Y397Z hPar1 (□), truncated hPar1 (Δ), and empty vector (▲ tumor volume 30±3 $mm^3$*P<0.005). FIG. 2D is a photograph of tissue sections taken from orthotopic mammary fat pad tumors generated by MCF7 cells over-expressing the various hPar1 constructs and stained with hematoxylin eosin (right panels). Magnification is ×100. Upper panel: Vector, second panel from the top: Truncated, third panel from the top: wild-type, lower panel: Y397Z.

FIG. 3A is a photograph showing sections of tumors generated by various hPar1 constructs and subjected to immunohistochemical staining with Ki-67 (upper panel), and with either an endothelial cell-specific lectin (α-lectin, mid-panel) or anti-CD31 (lower panel). FIG. 3B is a graph showing the mean (±SD) number of Ki-67-positive cells per high power field (HPF) as counted in five microscope fields per tumor section. FIG. 3C and FIG. 3D are graphs showing the mean (±SD) number of anti-lectin- or anti-CD31-stained cells, respectively, per high power field (HPF) as counted in five microscope fields per tumor section. Error bars show +/−SD of mean and the P value was determined (** P<0.005 * P<0.001; Chi-square test). The data are representative of four independent experiments performed in triplicates.

DETAILED DESCRIPTION OF EMBODIMENTS

Figure 1:
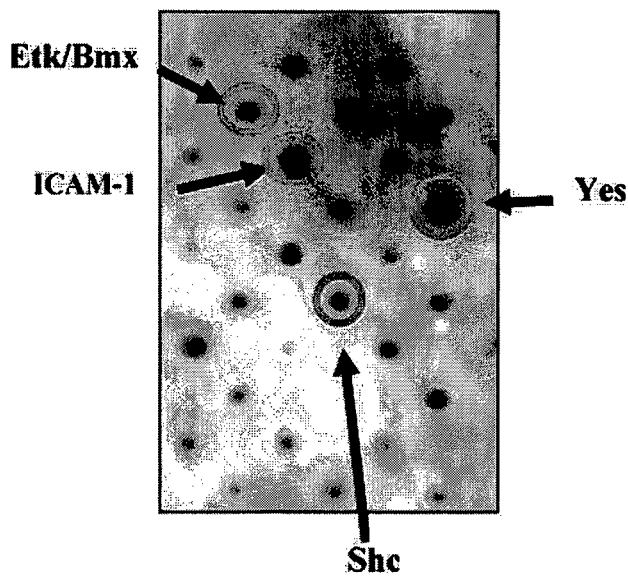
FIG. 1A is a table listing the antibodies in an antibody array which includes thirty antibodies directed against various proteins. The antibodies were immobilized on a membrane at a pre-determined position as illustrated in the table.
FIG. 1B is a photograph of the antibody array membrane showing specific protein-protein interactions between PAR1 and various signaling partners.

The present invention concerns isolated PAR1 cytoplasmic tail (c-tail) peptides and isolated PAR2 cytoplasmic tail (c-tail) peptides, as well as compositions comprising these peptides, uses thereof and methods of treating various diseases, in particular cancer.

The inventors of the present invention identified regions in the cytoplasmic portion of PAR1 and PAR2 that are responsible for signal transduction, specifically, regions which are responsible for the interaction with PH-domain containing proteins. The inventors also demonstrated that abrogation of the association between the cytoplasmic portion of PAR1 and PH-domain containing proteins (e.g. Etk) resulted in a reduction in PAR1 induced oncogenic activity, and that peptides of the invention effectively penetrate cells and interfere in the association between PAR1 and Etk.

Accordingly, the present invention includes peptides, pharmaceutical compositions and methods for alleviating pathological conditions which are mediated by or associated with PAR1 or PAR2 cellular pathways. In one embodiment the invention concerns peptides, pharmaceutical compositions and methods for treating cancer. Accordingly, a human or animal with cancer is administered with a pharmaceutical composition comprising an isolated peptide comprising an amino acid sequence of the PAR1 or PAR2 cytoplasmic tail, or a fragment or modification thereof, wherein the isolated peptide interferes with the binding reaction between PAR1 or PAR2 and a PH domain containing protein. The peptides may be administered alone or in combination with other therapeutic agents for the amelioration and/or treatment of cancer. The other therapeutic agents can be anti-angiogenic agents, anti-proliferative agents, growth inhibitory agents (e.g. chemotherapeutic agents).

As used herein, "isolated" or "purified" when used in reference to a peptide means that the peptide has been removed from its normal physiological environment (e.g. the peptide is present as such and not in the context of the complete protein, and not in its natural compartment, namely the peptide is isolated from the cell), or is synthesized in a non-natural environment (e.g. artificially synthesized in a heterologous system).

As used herein the term "PAR1" refers to protease-activated receptor 1. As used herein the term "PAR2" refers to protease-activated receptor 2. PAR1 and PAR2 have an amino-terminal exodomain and a carboxy-terminal cytoplasmic or endodomain.

The terms "PAR1 cytoplasmic tail" or "PAR2 cytoplasmic tail" (also referred to as "c-tail", "cytoplasmic portion" or "cytoplasmic domain") refer to the C-terminus (carboxy-terminus) of the PAR1 or PAR2 protein which is present within the cell cytoplasm and contains the signal binding region for downstream cellular signaling, as represented for example by SEQ ID NO:33.

As used herein the terms "PAR1 cytoplasmic tail (c-tail) peptide" or "PAR2 cytoplasmic tail (c-tail) peptide" refer to peptides having amino acid sequence that corresponds to portions of the cytoplasmic tail of PAR1 or PAR2, respectively.

As used herein the term "fragment or modification" with respect to the peptides of the invention refers to any variants or derivatives of these peptides.

The term "PH-domain containing protein" refers to proteins which include the pleckstrin homology (PH) domain. Proteins which are involved in signal transduction consist of several modular domains. These modules can confer catalytic or structural functions or mediate protein-protein interactions. One of these module domains is the pleckstrin homology (PH) domain which is identified as a 100 to 120 amino acid stretch in more than 250 human proteins (Rebecchi, M. J. and Scarlata, S. *Annu Rev Biophys Biomol Struct*, 1998. 27: p. 503-28). Although the amino acid sequence of PH domains is not universally conserved, the tertiary structure is remarkably conserved. PH-domain containing proteins can be identified using various available proteomic databases, e.g. the ExPASy proteomics server. Non-limiting examples of PH-domain containing proteins are Etk/Bmx, Akt/PKB, Vav, SOS 1 and GAB 1.

The epithelial tyrosine kinase (Etk), also known as Bmx, is a non-receptor tyrosine kinase that is unique by virtue of being able to interact with both tyrosine kinase receptors and GPCRs. This type of interaction is mainly attributed to the pleckstrin homology (PH) which is followed by the Src homology SH3 and SH2 domains and a tyrosine kinase site.

Akt, also known as PKB, is a serine/threonine protein kinase that plays a pivotal role in multiple cellular processes and ubiquitously expressed in a wide spectrum of cell types.

The $Vav_3$ oncogene, a guanine nucleotide exchange factor (GEF) for the Rho family GTPases, belongs to the Vav family proteins. The three mammalian proteins ($Vav_1$, $Vav_2$ and $Vav_3$) exhibit different tissue distribution. While $Vav_1$ is primarily expressed in hematopoeitic cells, $Vav_2$ and $Vav_3$ are more ubiquitously expressed. $Vav_3$ has been shown to be over-expressed in human prostate cancer as well as breast cancer.

The term "interfere in the binding reaction between PAR1 and a PH-domain containing protein" (e.g. with Etk/Bmx) refers to a reduction or elimination of the association between PAR1 and a downstream signaling PH-domain containing protein. Such an association is usually induced upon activation of PAR1. Similarly, the term "interfere in the binding reaction between PAR2 and a PH-domain containing protein" (e.g. with Etk/Bmx) refers to a reduction or elimination of the association between PAR2 and a downstream signaling PH-domain containing protein. Such an association is usually induced upon activation of PAR2. The ability of an agent to interfere in these binding reactions can be determined by methods known in the art. Some of these methods are exemplified in the Examples provided below.

The terms "pathological condition" or "disease" are commonly recognized in the art and designate the presence of at least one sign and/or symptom in a subject or a patient that are generally recognized as abnormal. Pathological conditions or diseases may be diagnosed and categorized based on pathological changes. Signs may include any objective evidence of a disease such as changes that are evident by physical examination of a patient or the results of diagnostic tests that may include, among others, laboratory tests. Symptoms are subjective evidence of disease or a patient condition, e.g. the patient's perception of an abnormal condition that differs from normal function, sensation, or appearance, which may include, without limitations, physical disabilities, morbidity, pain and other changes from the normal condition experienced by a subject.

Pathological conditions or diseases which are mediated by or associated with PAR1 or PAR2 cellular pathways include but are not limited to, cancer, acute and chronic inflammatory diseases, for example inflammatory diseases of the joints (e.g. arthritis), lungs (e.g. respiratory tract disorders such as pulmonary fibrosis, asthma and chronic obstructive pulmonary disease), brain, gastrointestinal tract (e.g. inflammatory bowel disease, such as colitis) and vascular systems (including cardiovascular diseases, e.g. thrombosis and restenosis), as well as inflammation associated with tissue response to injury. Also included are wound healing and pain, as well as allergies such as allergic contact dermatitis, atopic dermatitis and pruritus.

As used herein the term "Cancer" refers to any type of malignant proliferative disease and is used as commonly known in the art. In particular, the present invention concerns cancer types which are associated with PAR1 and/or PAR2 signal transduction and which can benefit from interfering with PAR1 and/or PAR2 signal transduction. Non limiting examples include breast cancer, ovary cancer, lung cancer, colon cancer, prostate cancer and melanoma.

The term "treating" refers to a reduction or elimination of at least one sign and/or symptom of a specific disease or condition. The term also encompasses prevention or attenuation of disease progression.

The term "agent" or "therapeutic agent" as used herein refers to a chemical entity or a biological product, or combination of chemical entities or biological products, which are used to treat, prevent or control a disease or a pathological condition.

As used herein, the term "therapeutically effective" includes both pharmacological effectiveness and physiological safety. Pharmacological effectiveness refers to the ability of the treatment to result in a desired biological effect in the patient. Physiological safety refers to the level of toxicity, or other adverse physiological effects at the cellular, organ and/or organism level (often referred to as side-effects) resulting from administration of the treatment.

Thus, in connection with the administration of an agent or a pharmaceutical composition, an agent or a pharmaceutical composition which are "effective against" a disease or pathological condition indicates that administration in a clinically appropriate manner results in a beneficial effect for at least a statistically significant fraction of patients, such as an improvement of symptoms, a cure, a reduction in disease signs or symptoms, extension of life, improvement in quality of life, or other effect generally recognized as positive by medical doctors familiar with treating the particular type of disease or condition.

The term "therapeutically effective amount" refers to a dosage or amount that is sufficient to reduce, halt, or slow disease progression to result in alleviation, lessening or amelioration of symptoms in a patient or to achieve a desired biological outcome, e.g. slow or stop tumor growth or reduction or disappearance of a tumor.

As used herein the term "patient" relates to a subject suffering from or suspected of suffering from a specific disease or pathological condition or presents with at least one sign of a specific disease or pathological condition. Preferably, the subject is a human subject.

"Pharmaceutically acceptable carriers or diluents" also referred to as pharmaceutically acceptable excipients or vehicles refer to a pharmaceutically acceptable material, composition or vehicle, suitable for administering compounds of the present invention to mammals, specifically to humans. These include for example, water, saline, glycerol, ethanol etc. Additionally, auxiliary substances, such as wetting or emulsifying agents, buffers, preservatives, anti-oxidants, surfactants, and the like, may be present in such carriers or diluents.

Examples of suitable "buffers" include Tris, Hepes, triethanolamine, histidine, or any others known in the art.

"Preservatives" can act to prevent bacteria, viruses, and fungi from proliferating in the pharmaceutical composition or formulation, and anti-oxidants can function to preserve the stability. Examples include octadecyldimethylbenzyl, ammonium chloride, hexamethonium chloride, benzalkonium chloride, and benzethonium chloride. Other types of compounds include aromatic alcohols such as phenol and benzyl alcohol, alkyl parabens such as methyl or propyl paraben, and m-cresol.

A "surfactant" can act to decrease turbidity or denaturation of a protein or a peptide in a pharmaceutical composition or formulation. Examples of surfactants include non-ionic surfactant such as a polysorbate, e.g. polysorbates 20, 60, or 80, a poloxamer, e.g. poloxamer 184 or 188, Pluronic polyols, ethylene/propylene block polymers or any others known in the art.

The peptides of the invention or the pharmaceutical compositions of the invention may be used in combination with other therapeutic agents. "Use in combination" as used herein refers to the administration with at least one other therapeutic agent, either at the same time, in the same composition, at alternating times (prior to or subsequent to), in separate compositions, or combinations thereof.

The inventors have identified PAR1 and PAR2 C-tail as a scaffold site for the interaction with signaling partners. In addition to identifying key partners, the hierarchy of binding was determined and a specific region in PAR1 C-tail was identified as critical for breast cancer signaling. Specifically, Etk/Bmx and Shc were found to form a physical complex with PAR1 C-tail. Etk/Bmx was shown to bind to PAR1-C-tail via its PH domain enabling the subsequent association of Shc. The physiological significance of PAR1-Etk/Bmx binding is emphasized by inhibition of Matrigel invasion and appearance of nearly intact acini morphogenesis of cell architecture when this site is mutated to abrogate the binding of Etk/Bmx. The use of consecutive A residues inserted into the proposed Etk/Bmx binding region of PAR1 C-tail (e.g., hPar1-7A) abolished PAR1-induced pro-oncogenic properties. Thus, by preventing the binding of a key signaling partner to PAR1 C-tail, efficient inhibition of PAR1-induced tumor-associated functions, including loss of epithelial cell polarity, migration and invasion through basement membranes, is obtained.

The inventors also identified an amino acid sequence at the C-tail of PAR2 which is responsible for the interaction with Etk/Bmx as well as additional PH-domain containing proteins.

In one of its aspects, the present invention thus provides isolated peptides corresponding to the PAR1 cytoplasmic tail or any fragment thereof, more specifically peptides corresponding to the "signal-binding" region in the cytoplasmic tail. The PAR1-Etk/Bmx binding motif sequence was found to be: NH2-CQRYVYS-COOH. Therefore, in one embodiment the present invention provides a peptide comprising the amino acid sequence CQRYVYS (SEQ ID NO: 1) or any fragment or modification thereof that maintains the ability to interfere in the binding reaction between PAR1 and Etk/Bmx.

In one embodiment, the present invention provides a peptide having 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, 23 or more, 24 or more, and 25 or more amino acids comprising the amino acid sequence CQRYVYS or any fragment or modification thereof.

In one embodiment, the present invention provides a peptide having between about 7 and about 25 amino acids comprising the amino acid sequence CQRYVYS or any fragment or modification thereof.

In one embodiment said peptide is 12 amino acids long. In a specific embodiment said peptide consists of the sequence NH2-SSECQRYVYSIL-COOH (SEQ ID NO: 3), or any fragment or modification thereof that maintains the ability to interfere in the binding reaction between PAR1 and Etk/Bmx. In another embodiment said peptide is 15 amino acids long. In a specific embodiment said peptide consists of the sequence NH2-SSECQRYVYSILCCK-COOH (SEQ ID NO: 4) or any fragment or modification thereof that maintains the ability to interfere in the binding reaction between PAR1 and Etk/Bmx.

Without wishing to be bound by theory, longer peptides (i.e. peptides longer than 7 amino acids, or longer than 8 amino acids, or longer than 9 amino acids, or longer than 10 amino acids, or longer than 11 amino acids) may have preferable characteristics such as better solubility or stability as compared with shorter peptides (e.g. peptides having 7 amino acids or 8 amino acids).

In another of its aspects, the present invention provides isolated peptides corresponding to the PAR2 cytoplasmic-tail, or any fragment thereof, more specifically peptides corresponding to the "signal-binding" region in the cytoplasmic tail. The PAR2-Etk/Bmx binding motif sequence was found to be: NH2-SHDFRDHA-COOH. In one embodiment the present invention provides a peptide having 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, 23 or more, 24 or more, and 25 or more amino acids comprising the amino acid sequence SHDFRDHA or any fragment or modification thereof that maintains the ability to interfere in the binding reaction between PAR2 and Etk/Bmx.

In one embodiment, the present invention provides a peptide having between about 8 and about 25 amino acids comprising the amino acid sequence SHDFRDHA (SEQ ID NO: 2) or any fragment or modification thereof.

In one embodiment said peptide is 15 amino acids long.

Preferably, the peptides of the invention are designed so as to penetrate cell membranes. In certain embodiments, cell penetrating moieties or membrane tethering moieties may be attached to the peptides of the invention in order to allow cell membrane penetration. Cell penetrating moiety is a compound which mediates transfer of a substance from an extracellular space to an intracellular compartment of a cell. Cell penetrating moieties shuttle a linked substance into the cytoplasm or the cytoplasmic space of the cell membrane. Membrane tethering moieties are compounds which associate or bind to a cell membrane. Thus the membrane tethering moiety brings the substance to which the membrane-tethering moiety is attached in close proximity to the membrane of a target cell. For example, cell penetrating moieties or membrane tethering moieties may be hydrophobic moieties. A cell penetrating moiety and a membrane tethering moiety includes, but is not limited to, a lipid, cholesterol, phospholipids, steroid, or a fatty acid moiety. Cell penetrating moieties may also be Cell Penetrating Peptides (CPP) such as Tat (trans-activating transcriptional activator from HIV-1) or Penetratin™ (Penetratin™ 1 is a 16-amino acid peptide corresponding to the third helix of the homeodomain of Antennapedia protein), or small molecule synthetic analogues of CPP. The cell penetrating moiety or membrane tethering moiety is attached to the C-terminal amino acid, the N-terminal amino acid, or to an amino acid between the N-terminal and C-terminal amino acid of the peptide of the invention.

The peptides of the invention may also be modified in manners which increase their solubility, stability or half-life in the body (e.g. modifications which reduce proteolytic degradation of the peptide upon administration to the patient, or reduce the clearance from the blood). These modifications include, but are not limited to association with stabilizing molecules, e.g. pegylation, encapsulation (for example in lyposomes) using methods well known in the art.

The present invention also encompasses peptidomimetics, i.e. any peptides or other types of agents which mimic the activity of the peptides of the invention. The present invention is therefore contemplated to include any variants, derivatives, fragments or modifications of the peptides of the invention. These variants, derivatives, fragments or modifications maintain the activity of the original peptide. In certain embodiments, the variants, derivatives, fragments or modifications of the peptides of the invention are active in vivo or in vitro in interfering in the binding reaction between PAR1 or PAR2 and a PH-domain containing protein, e.g. Etk/Bmx.

In certain embodiments the variants, derivatives, fragments or modifications are biologically active and have at least about 80% amino acid sequence identity, more preferably at least about 90% sequence identity, and even more preferably, at least 95%, 96%, 97%, 98%, or 99% sequence identity with any one of the above recited PAR1 or PAR2 c-tail peptides.

"Percent (%) amino acid sequence identity" with respect to the sequences identified herein is defined as the percentage of amino acid residues in a candidate sequence that are identical with the amino acid residues in the PAR1 or PAR2 c-tail peptides sequences, after aligning the sequences and introducing gaps, if necessary, to achieve the maximum percent sequence identity, and not considering any conservative substitutions as part of the sequence identity. Alignment for the purposes of determining percent amino acid sequence identity can be achieved in various ways that are well known in the art.

Accordingly, various modifications may be made in the peptides of the invention. Mutations may be inserted in the identified binding region by site-directed mutagenesis e.g. by using QuickChange kit (Stratagene, La Jolla, Calif.). The binding capabilities of naïve wt protein can then be compared with proteins comprising the mutated domain.

For example, an alanine scan can be used to identify the residues that are critical for PAR1 "signal binding". Different peptides are produced each having an alanine residue in a different position, for example as follows:

```
                                            (SEQ ID NO: 5)
            NH2-SSECQRYVYSILCCA-COOH (SEQ ID NO: 6)
            NH2-SSECQRYVYSILCAK-COOH (SEQ ID NO: 7)
            NH2-SSECQRYVYSILACK-COOH (SEQ ID NO: 8)
            NH2-SSECQRYVYSIACCK-COOH (SEQ ID NO: 9)
            NH2-SSECQRYVYSALCCK-COOH (SEQ ID NO: 10)
            NH2-SSECQRYVYAILCCK-COOH (SEQ ID NO: 11)
            NH2-SSECQRYVASILCCK-COOH (SEQ ID NO: 12)
            NH2-SSECQRYAYSILCCK-COOH (SEQ ID NO: 13)
            NH2-SSECQRAVYSILCCK-COOH (SEQ ID NO: 14)
            NH2-SSECQAYVYSILCCK-COOH (SEQ ID NO: 15)
            NH2-SSECARYVYSILCCK-COOH (SEQ ID NO: 16)
            NH2-SSEAQRYVYSILCCK-COOH (SEQ ID NO: 17)
            NH2-SSACQRYVYSILCCK-COOH (SEQ ID NO: 18)
            NH2-SAECQRYVYSILCCK-COOH (SEQ ID NO: 19)
            NH2-ASECQRYVYSILCCK-COOH
```

Next, in order to improve the peptide inhibitory activity the non-essential residues identified in the ala scan can be replaced with other amino acid residues, optionally by non-natural amino acids.

The following are non-limiting examples of mutations that may be inserted in PAR2: wt C-tail-SHDFRDHAZ (SEQ ID NO:20); mutated forms of PAR2 C-tail-SAAARDHAZ (SEQ ID NO:21); or SHDFAAAAZ (SEQ ID NO:22). For these exemplary mutations the following primers may be used:

```
Primer1:
                                                    (SEQ ID NO: 23)
F-cccctttgtctattactttgtttcagctgctgccagggatcatg;

(SEQ ID NO: 24)
R-gcatgatccctggc agcagctgaa acaaagtaa tagacaaagggg;

Primer2:
                                                    (SEQ ID NO: 25)
F-cacatgatttcgcggctgc tgcaaagaacgctc tcctttgccg;

(SEQ ID NO: 26)
R-cggcaaag gagagcgttctttgcagca gccgcgaaatcatgtg;
```

Chemical modifications can also be made in the peptides. For example, relevant amino acids (e.g., leucine, isoleucine) may be modified to include alternative side chains, non-limiting examples of such side chains include: ethyl, n-butyl, —$CH_2CH_2OH$, —$CH_2CH_2CH_2OH$, —$CH_2CHOHCH_3$ and —$CH_2SCH_3$. Tyrosine amino acid can be modified by having substituted benzyl or phenyl side chains. Preferred substituents include one or more of the following: halogen, methyl, ethyl, nitro, methoxy, ethoxy and —CN.

Glutamic acid may be modified to substituted or unsubstituted aliphatic, aromatic or benzylic ester of glutamic acid (e.g., methyl, ethyl, n-propyl iso-propyl, cyclohexyl, benzyl or substituted benzyl), glutamine, CO—NH-alkylated glutamine or asparagine (e.g., methyl, ethyl, n-propyl and iso-propyl) and modified amino acids having the side chain —$(CH_2)_3COOH$, an ester thereof (substituted or unsubstituted aliphatic, aromatic or benzylic ester), an amide thereof and a substituted or unsubstituted N-alkylated amide thereof.

For lysine or arginine amino acids modification will be carried out by 1 to about 3 additional methylene units in the side chain.

The amino acids serine and cysteine may be modified having $C_1$-$C_5$ straight or branched alkyl side chains substituted with —OH or —SH.

The term "chemical modification" as used herein includes modification at the side chain of the amino acid residue, as well as modification of the peptidic bond. Accordingly, a functional group may be added to the side chain, deleted from the side chain or exchanged with another functional group. Typically, the modifications are conservative modifications resulting in conservative substitution. Examples of conservative modifications of this type include adding an amine or hydroxyl, carboxylic acid to the aliphatic side chain of valine, leucine or isoleucine, exchanging the carboxylic acid in the side chain of aspartic acid or glutamic acid with an amine or deleting the amine group in the side chain of lysine or ornithine. Other chemical modifications known in the art include arboxymethylation, acylation, phosphorylation, glycosylation or fatty acylation, and others.

The "chemical modification" also includes alteration of a bond within the peptidic backbone, i.e. that the bond between the N— of one amino acid residue to the C— of the next has been altered to non-naturally occurring bonds by reduction (to —$CH_2$—NH), alkylation (methylation) on the nitrogen atom, or the bonds have been replaced by amidic bond, urea bonds, or sulfonamide bond, etheric bond (—$CH_2$—O—), thioetheric bond (—$CH_2$—S—), or to —C—S—NH—; The side chain of the residue may be shifted to the backbone nitrogen to obtain N-alkylated-Gly (a peptidoid). Modification also includes cyclization of the amino acid molecule, e.g. by forming S—S bonds. S—S bonds may be formed via the inclusion of sulphor-containing amino acid residues, such as cysteine at each terminus of the amino acid molecule. Cyclic peptides have been shown to be more stable and with higher biological activity than the corresponding linear molecule (Jining L. et al. *Eur. J. Biochem* 271:2873-2886 (2004)).

The peptides of the invention may be provided in a soluble or a lyophilized (dry) form.

The peptides of the invention can be prepared by automated peptide synthesis methodologies well known in the art.

Alternatively the PAR1 or PAR2 c-tail peptides of the invention may be isolated from the complete PAR1 or PAR2 protein, respectively, preferably, the human PAR1 or PAR2 protein. Isolation from the complete PAR1 or PAR2 protein can be effected, for example, by proteolysis of PAR1 or PAR2 by proteases such as thrombin, plasmin, activated protein C, or metalloprotease-1.

Alternatively, the PAR1 or PAR2 c-tail peptides of the invention may be produced recombinantly using methods well known in the art.

In another aspect, the present invention provides a method of inhibiting PAR1 mediated signal transduction comprising administering an agent capable of selectively inhibiting the binding of PAR1 and a PH-domain containing protein, e.g. Etk/Bmx, vav3 or Akt.

In another aspect, the present invention provides a method of treating a disease comprising administering a therapeutically effective amount of an agent capable of selectively inhibiting the binding of PAR1 and a PH-domain containing protein, or a pharmaceutical composition comprising said agent.

In a specific embodiment the PH-domain containing protein is Etk/Bmx.

In other embodiments the PH-domain containing protein is vav3 or Akt.

The invention is not limiting with respect to the type of agent that inhibits or interferes with the binding between PAR1 and the PH-domain containing protein. The agent may be, but is not limited to, a peptide, a peptidomimetic molecule, a polypeptide, or a small molecule (e.g. a chemical compound). In a specific embodiment the agent is a peptide.

The invention further provides a method of treating a disease comprising administering a therapeutically effective amount of a peptide, or a pharmaceutical composition comprising the peptide, to a patient in need thereof, wherein the peptide is selected from the group consisting of:

(a) An isolated PAR1 c-tail peptide comprising the amino acid sequence CQRYVYS (SEQ ID NO: 1);
(b) an isolated PAR1 c-tail peptide consisting of the sequence SSECQRYVYSIL (SEQ ID NO: 3);
(c) An isolated PAR1 c-tail peptide consisting of the amino acid sequence SSECQRYVYSILCCK (SEQ ID NO: 4); and
any fragment or modification of the peptides of (a) (b) or (c).

PAR1 has been shown to play a central role in the invasive and metastatic cancers of breast, ovaries, lung, colon, prostate and melanoma. Therefore, in a specific embodiment the invention is directed to a method of treating cancer.

In certain embodiments the cancer is selected from the group consisting of breast cancer, ovary cancer, lung cancer, colon cancer, prostate cancer and melanoma.

In another aspect, the present invention provides a method of inhibiting PAR2 mediated signal transduction comprising administering an agent capable of selectively inhibiting the binding of PAR2 and a PH-domain containing protein, e.g. Etk/Bmx, vav3 or Akt.

In another aspect, the present invention provides a method of treating a disease comprising administering a therapeutically effective amount of an agent capable of selectively inhibiting the binding of PAR2 and a PH-domain containing protein, or a pharmaceutical composition comprising said agent.

In a specific embodiment the PH-domain containing protein is Etk/Bmx.

In other embodiments the PH-domain containing protein is vav3 or Akt.

The invention is not limiting with respect to the type of agent that inhibits or interferes with the binding between PAR2 and the PH-domain containing protein. The agent may be, but is not limited to, a peptide, a peptidomimetic molecule, a polypeptide, or a small molecule (e.g. a chemical compound). In a specific embodiment the agent is a peptide.

The invention further provides a method of treating a disease comprising administering a therapeutically effective amount of a peptide, or a pharmaceutical composition comprising the peptide to a patient in need thereof, wherein the peptide is selected from the group consisting of:
  (a) An isolated PAR2 c-tail peptide comprising the amino acid sequence SHDFRDHA (SEQ ID NO: 2); and
  (b) any fragment or modification of the peptide of (a).

In a specific embodiment the invention is directed to a method of treating cancer.

In certain embodiments the cancer is selected from the group consisting of breast cancer, ovary cancer, lung cancer, colon cancer, prostate cancer and melanoma.

In another embodiment, the present invention provides a pharmaceutical composition comprising a peptide of the invention together with a pharmaceutically acceptable carrier or diluents.

In another embodiment, the present invention provides use of a peptide of the invention in the preparation of a pharmaceutical composition.

In certain embodiments said pharmaceutical composition is for the treatment of cancer.

In one embodiment the present invention provides a combination of PAR1 c-tail peptides and PAR2 c-tail peptides of the invention. This combination of peptides may be used as a therapeutic agent for the treatment of cancer.

Any of the peptides, pharmaceutical compositions or methods of the invention may used in combination with additional therapeutic agents, e.g. for the treatment of cancer.

Example 1

Materials and Methods
Cell Culture:
MCF7 and MDA-MB-435 human breast carcinoma, CT-26 mouse colon carcinoma, HEK-293 cells and the African green monkey kidney fibroblast cell line COS1 (obtained from the ATCC, VA, USA) were maintained in DMEM with 10% fetal calf serum. Stable clonal cell lines over-expressing wt hPar1, Y397Z hPar1, truncated hPar1 and Y/A mutants; $Y_{381}A\&_{383}A$ hPar1 or the wt-Etk and Etk-KQ were selected for G418 resistance (800 µg/ml).

Plasmids and Transfection:
MCF7 cells were transfected with 1-2 µg of either wt human hPar1 or truncated hPar1 or Y397Z hPar1 cDNA, or with a control pcDNA3 vector (Invitrogen, Carlsbad, Calif.) using FuGene transfection reagent (Roche Molecular Biochemicals, Indianapolis, Ind.). Transfected cells were selected with G418 (800 µg/ml) to obtain stable populations of cells expressing hPar1 and the variants. Etk/Bmx plasmids (e.g., wt, kinase-dead, KQ and GST-PH-Etk/Bmx) (Tsai Y T, et al. (2000) *Mol Cell Biol.* 20:2043-2054.) were transfected into HEK-293 cells using the same protocol as previously described.

RNA Isolation and RT-PCR.
RNA was isolated with Tri-Reagent (MRC, Cincinnati, Ohio) according to the manufacturer's instructions. After reverse transcription of 1 µg total RNA by oligo (dT) priming, cDNA was amplified using Taq DNA polymerase (Promega, Madison, Wis.). Comparative semi-quantitative PCR was performed using the following primers: GAPDH sense: 5'-CCA CCC ATG GCA AAT TCC ATG GC-3' (SEQ ID NO: 27) and antisense: 5'-TCT AGA CGG CAG GTC AGG TCC ACC-3' (SEQ ID NO: 28) primers. $PAR_1$ N-terminus primers were as follows: hPar1-sense: 5'-CTCGTC-CTCAAGGAGCAAAC-3' (SEQ ID NO: 29), antisense orientation: 5'-TGGGATCGGAACTTTCTTTG-3' (SEQ ID NO: 30) (resulting in a 564-bp PCR product). $PAR_1$ C-tail primers-sense: 5'-TAC TAT TAC GCT GGA TCC TCT GAG-3' (SEQ ID NO: 31) and antisense: 5'-CTT GAA TTC CTA AGT TAA CAGCTT-3' (SEQ ID NO: 32). These primers give rise to a 181-bp product corresponding to the entire $PAR_1$ C-tail site, as follows:

(SEQ ID NO: 33)
YYYASSECQRYVYSILCCKESSDPSYNSSGQLMASKMDTCSSNLNNSI

YKKLLT.

Animal Studies: Mammary Gland Model.
Female athymic nude mice at 6-8 weeks of age were pre-implanted subcutaneously with pellets containing 1.7 mg β-estradiol (60-day release, Innovative Research of America, Sarasota, Fla.). Mouse mammary fat pads were then injected with $1\times10^7$ MCF-7 cells stably transfected with hPar1 wt and mutant constructs (e.g., Y397Z and truncated) or pcDNA3 control plasmid. Mice were monitored for tumor size by external caliber measurements (length and width) on days 10, 22, 25, 29, 33, 36 and 45. Tumor volume (V) was calculated by $V=L\times W2\times 0.5$, where L is length and W is width. On day 45, mice were sacrificed and tumors were removed, weighed and fixed in formalin for histology. All animal experiments were approved by the animal committee of the Hebrew University, Jerusalem, Israel (MD-107.05-4).

Liver Metastasis Model:
CT-26 mouse colon carcinoma cells were stably transfected with either wt hPar1 or hPar1-$Y_{381}$A constructs. The activation of $PAR_1$ (using the peptide SFLLRN) was performed prior to injection into the mice. CB6F1 mice were anesthetized (75 mg/kg ketamine+3 mg/kg xylazine, i.p.), and the spleen was exteriorized through an incision (1.0 cm) on the left side of the mouse. CT-26 cells ($10^4$ cells/mouse) transfected with the different constructs (e.g., hPar1, hPar1 Y381A, mock-transfected vector) were injected into the spleen using a 30-gauge needle. The cell suspension was allowed to enter the portal circulation over a short period (5 minutes), after which the spleen was removed, as previously described (Kuruppu D, et al (2002) *J Surg Res.* 103:47-54.). The wound was sutured and the animal was allowed to recover. MRI images were monitored every 2-3 days on a 4.7T Bruker Biospec spectrometer using a bird-cage coil. Tumor assessment was made by serial coronal and axial $T_2W$ fast SE images (TR/TE=2000/40 ms). All experiments were performed in accordance with the guidelines of the Animal Care and Use Committee of the Hebrew University, Jerusalem, Israel (MD-107.05-4).

PAR$_1$ Activation:

PAR$_1$ was activated by the SFLLRN(H-Ser-Phe-Leu-Leu-Arg-Asn-NH$_2$) peptide (SEQ ID NO: 34), the TFLLRN-PNDK peptide (SEQ ID NO: 35), a selective PAR$_1$ agonist, or thrombin (1 U/ml).

Histology:

Tissue samples derived from the primary tumors were fixed with 4% formaldehyde in PBS, embedded in paraffin and sectioned (5-µm sections). After de-paraffinization and re hydration, sections were stained with hematoxylin and eosin (H&E) or subjected to immunohistochemistry using specific antibodies.

Histological Evaluation and Scoring:

The combined histological results were assessed and scored as previously described (Groeger A M, et al. (2004) *Histopathology* 44:54-63). The measurements per slide section were carried out using anatomical compartments, using an ocular micrometer (WHIOX2, Olympus, N.J., USA). Slides review was independently performed by two investigators (BM and RB). Discrepancies were resolved by simultaneous re-examination of the slides by both investigators using a double-headed microscope. The microscope was calibrated with a micrometer slide before each measurement. All measurements were performed on the monitor screen using a ×40 objective. On examining the sections for selection of fields tumor cells from the most cellular area at the center of the tumor were selected. Necrotic and inflammatory area were avoided. Eight microscopic fields were screened, 10 cells/field were selected and no less than 50 cells/tumor case were assessed. The positive rate of staining is expressed as a mean±SD per tumor histological subtype from selected cases.

Immunohistochemistry.

Sections were subjected to inactivation of endogenous peroxidase (3% H$_2$O$_2$ in DDW), antigen retrieval by microwave oven (3 min) in citrate buffer (0.01 M, pH 6.0), and blocking with 10% goat serum in PBS. Sections were then incubated with antibodies directed against Von-Willebrand factor (anti-factor VIII, DAKO, Carpinteria, Calif.), Ki-67 (Clone SP6, Lab Vision-NeoMarkers, Fremont, Calif.), or an endothelial cell-specific lectin (*Bandeiraea simplicifolia* BS-1 isolation), followed by incubation with horseradish peroxidase-conjugated anti-rabbit antibody (DAKO, Carpinteria, Calif.). Color was developed by incubation (10 min) with the Zymed AEC substrate kit (Zymed Laboratories, South San Francisco, Calif.), and counterstained with Mayer's hematoxylin.

Preparation of hPar1 Constructs: Truncated hPar1, Y397Z hPar1, Y$_{381}$A hPar1 and Y383A hPar1.

Detection of hPar1 was carried out using primers: sense orientation: 5'-CTCGTCCTCAAGGAGCAAAC-3' (SEQ ID NO: 29), antisense orientation: 5'-TGGGATCG-GAACTTTCTTTG-3' (SEQ ID NO: 30). For the PAR$_1$-C-tail primers: sense orientation: 5'-TACTATTACGCTG-GATCCTCTGAG-3' (SEQ ID NO: 31), antisense: 5'-(SEQ ID NO: 33).

Using polymerase chain reaction, a PAR-1 mutant protein truncated in its cytoplasmic tail after amino acid leucine 369 or at tyrosine 397 was constructed. Y397Z construct: PAR-1 cDNA served as a template for amplifying the fragment containing STOP codon using the followed primers: sense: 5'-ATA AGC ATT GAC CGG TTT CTG-3' (SEQ ID NO: 36) and antisense: 5'-GCT CTA GAT TTT AAC TGC TGG GAT CGG AAC-3' (SEQ ID NO: 37). Replacement of tyrosine residues at PAR$_1$ cytoplasmic tail was achieved using specific primers containing the point mutation. Primer sequences were as follows: 381-sense: 5'-TGC CAG AGG GCT GTC TAC AGT ATC TTA TGC-3' (SEQ ID NO: 38), 381-antisense: 5'-GAT ACT GTA GAC AGC CCT CTG GCA CTC AGA-3' (SEQ ID NO: 39), 383-sense: 5'-GCC AGA GGT ACG TCG CAA GTA TCT TAT GCT GCA AA-3' (SEQ ID NO: 40), 383-antisense: 5'-AAG ATA CTT GCG ACG TAC CTC TGG CAC TCA G-3' (SEQ ID NO: 41). The amplified DNA fragment was digested with XbaI and HindIII from PAR$_1$ cDNA and cloned into a pcDNA3 plasmid, followed by DNA sequencing. To confirm the functional integrity of the DNA constructs, wt and mutant cDNAs were transiently expressed in COS-1 cells that were subsequently subjected to FACS analysis with a PAR-1-specific antibody (WEDE15-PE, Immunotech, Cedex, France).

HA-tag wt hPar1 and HA-mutant hPar1-7A C-tail Constructs.

The mutants were designed for insertion of A at the carboxy terminus of PAR$_1$ residues 378-384: SSE CQRYVYSILCC (SEQ ID NO: 42) to SSEAAAA-AAAILCC (named hPar1-7A mutant) (SEQ ID NO: 43). For HA-tag wt hPar1 construct PCR primers were designed and added downstream to the ATG start codon. Primers for the HA-tag are as follows: sense: 5'-TAC CCA TAC GAT GTT CCA GAT TAC GCT-3' (SEQ ID NO: 44) and anti-sense: 5'-AGC GTA ATC TGG AAC ATC TA TGG GTA-3' (SEQ ID NO: 45). Replacement of seven residues with Ala (A) at positions 378-384 was made by synthesis of oligos containing the mutation. Primer sequences were as follows: hPar1 7A mutant: sense: 5'-TCT GAG GCT GCT GCT GCT GCT GCA GCT ATC TTA-3' (SEQ ID NO: 46) and anti-sense: 5'-TAA GAT AGC TGC AGC AGC AGC AGC AGC CTC AGA-3' (SEQ ID NO: 47). PCR products were then used as primers on an hPar1 cDNA template to create an extended product of introduced mutations into the full-length sequence. The amplified DNA fragment was digested with PinAI and XbaI from PAR$_1$ cDNA and cloned into pcDNA3-hPar1 plasmid followed by DNA sequencing.

GST-C-tail Cloning.

GST-C-tail of PAR$_1$ fragment, containing 54 amino acids from serine 369 to residue 425, was prepared using RT-PCR (5'-TAC TAT TAC GCT GGA TCC TCT GAG-3' (SEQ ID NO: 48) and 5'-CTG AAT TCC TAA GTT AAC AGC TT-3' (SEQ ID NO: 49)). The resulting DNA fragment was further cut with the appropriate restriction enzymes (BamHI and EcoR1) and ligated into pGEX2T vector. The GST-C-tail was separated by SDS-PAGE, which indicated that the fusion protein of the C-tail was adequately prepared. The molecular weight of GST protein is 27 kD and the GST-C-tail fusion protein is 32 kD. GST-Shc-SH2 and tandem SH2 were kindly provided by S. Katzav, Hubert H. Humphrey Center for Experimental Medicine and Cancer Research, Hebrew University-Hadassah Medical School, Jerusalem.

GST Fusion Protein Columns.

Fusion proteins were purified from transformed *Escherichia coli* bacteria that had been stimulated with isopropyl-β-D-thio-galactopyranoside (IPTG) at a concentration of 0.3 µM. Bacteria were lysed according to published procedures, and then immobilized on glutathione Sepharose beads (Pharmacia). Briefly, MDA-MB-435 cell lysates were applied to GST-PAR1 C-tail or GST control columns. After 2 h binding periods to the designated protein/s cell lysates to the columns, a washing step was performed. The washes (×3) were carried out using a "wash buffer" including: 100 mM NaCL, 20 mM EDTA, 10 mM Tris, pH 8.0 and 1% Triton ×100. This step was performed in order to wash out all non-specific proteins, leaving the GST-PAR$_1$-C-tail column firmly bound to targeted cell lysate proteins. Next, elution of bound proteins was performed via the addition of gel "sample buffer" and appropriate boiling. The samples were run electrophoretically on SDS-PAGE gels, followed by immunoblotting with the indicated antibodies and ECL detection.

GST-PH-Etk/Bmx.

The PH domain in Etk/Bmx was bound to GST column as previously described (Chen R, et al. (2001) *Nat Cell Biol.* 3: 439-444).

Purification of PAR$_1$ C-tail Fragments.

PAR$_1$ C-tail fragments were generated using a "thrombin cleavage capture kit" (Novagen, Madison, Wis.; Cat no. 69022-3). The enzyme used for the cleavage was biotinylated human thrombin. Briefly, the cleavage was performed according to the manufacturer instructions. Biotinylated thrombin was removed from the cleavage reaction using streptavidin agarose beads, and the cleaved peptides (e.g., wt PAR$_1$-C-tail and Y381A C-tail) were isolated and loaded on a GST-Etk-PH column. After incubation for 4 h the purified fragments were applied onto the GST-PH-Etk/Bmx column and detected following gel separation and western blotting analysis using anti-PAR$_1$ antibodies (ATAP, Santa Cruz, Calif.).

Flow Cytometry Analysis.

To activate PAR$_1$, thrombin (1 U/ml was added for 5 min. The cells were detached from the plates with 0.5 mM EDTA in 0.1 M sodium phosphate at pH 7.4 (Biological Industries), washed and re-suspended in PBS. The cells were analyzed by FACS after incubation for 60 min at 4° C. with 10 μg/ml anti-PAR$_1$-wede-PE antibodies.

Western Blot and Immunoprecipitation Analysis:

Cells were activated with agonist peptide TFLLRNPNDK (SEQ ID NO: 35) for the indicated periods of time and solubilized in lysis buffer containing 10 mM Tris-HCl, pH 7.4, 150 mM NaCl, 1 mM EDTA, 1% TritonX-100, and protease inhibitors (5 mg/ml aprotinin, 1 mM phenylmethylsulfonylfluoride, and 10 mg/ml leupeptin) at 4° C. for 30 min. The cell lysates were subjected to centrifugation at 12,000 rpm at 4° C. for 20 min. We used 400 μg of the supernatants with anti-PAR$_1$ (ATAP, Santa Cruz, Calif. 1 μg), anti-HA (anti-HA sc-7392; Santa Cruz, Calif.), anti-Shc or Etk/Bmx antibodies (10 μg/ml). After overnight incubation, Protein A-Sepharose beads (Amersham Pharmacia Biotech, Buckinghamshire, UK) were added to the suspension (50 μl), which was rotated at 4° C. for 1 h. The immunocomplexes were eluted and run electrophoretically on a 10% SDS-PAGE gel, followed by transfer to an Immobilon-P membrane (Millipore). Membranes were blocked and probed with 1 μg/ml amounts of the appropriate antibodies as follows: anti-PAR$_1$ thrombin receptor mAb, (ATAP, from Santa Cruz, 1:1000); anti-Shc (BD, 1:2000); anti-Bmx (Transduction Laboratories, 1:1000) or anti-PY (Upstate 4G10, 1:2500), suspended in 3% BSA in 10 mM Tris-HCl, pH 7.5, 100 mM NaCl, and 0.5% Tween-20. After washes the blots were incubated with secondary antibodies conjugated to horseradish-peroxidase. Immunoreactive bands were detected by enhanced chemiluminescence (ECL). Membranes were stripped and incubated with anti-IP antibodies to ensure equal protein load.

Anti-PAR$_1$ polyclonal antibodies were generated using two regions of the N-terminus portion R/SFFLRN by the synthetic peptides NH$_2$-CLLRNPNDKYEPFWED-COOH (SEQ ID NO: 50) and NH$_2$-KSSPLQKQLFAFISC-COOH (SEQ ID NO: 51).

Antibody Array:

A custom-made antibody array (hypromatrix) containing thirty antibodies against various proteins was prepared (FIG. 1). The antibodies were immobilized on a membrane, each at a pre-determined position, while retaining their capabilities of recognizing and capturing antigens as well as antigen-associated proteins. MDA-MB-435 cells were activated for 10 min with thrombin (1 U/ml). Untreated or activated cells were lysed with Triton extraction solution: 15 mM Tris, pH 7.5, 120 mM NaCl, 25 mM KCl, 2 mM EGTA, 2 mM EDTA, 0.1 mM DTT, 0.5% Triton X-100, 10 leupeptin and 0.5 mM PMSF. Protein extract was incubated on pre-blocked membrane for 2 h at room temperature. The antibody array was washed with TBST and incubated with biotinylated PAR$_1$ antibody (ATAP) for 2 h at room temperature. The antibody array was washed again with TBST, and the membrane was incubated with HRP-conjugated streptavidin for 1 h. Protein-protein interactions were detected by ECL and exposure to X-ray film.

Matrigel Invasion Assay:

Blind-well chemotaxis chambers with 13-mm diameter filters were used for this assay. Polyvinylpyrrolidone-free polycarbonate filters, 8 mm pore size (Costar Scientific Co., Cambridge, Mass.), were coated with basement membrane Matrigel (25 μg/filter). Briefly, the Matrigel was diluted to the desired final concentration with cold distilled water, applied to the filters, and dried under a hood. Cells ($2 \times 10^5$) suspended in DMEM containing 0.1% bovine serum albumin were added to the upper chamber. Conditioned medium of 3T3 fibroblasts was applied as a chemo-attractant and placed in the lower compartment of the Boyden chamber. Cells were incubated for 18 h on filters at 37° C. in 5% CO$_2$. At the end of the incubation, cells on the upper surface of the filter were removed by wiping with a cotton swab. The filters were fixed and stained with DifQuick System (Dade Behring Inc., Newark, N.J.). Ten fields were chosen from the lower surface of the filter and cells within each field were counted. The mean+/−SD of the ten fields was calculated for each filter. Each assay was performed in triplicate.

MCF10A Morphogenesis Assay:

MCF10A cells were maintained in DMEM/F12 medium with 20% donor horse serum. The cells for spheroid assay (DMEM/F12 supplemented with 2% donor horse serum, 10 μg/ml insulin, 1 ng/ml cholera-toxin, 100 lag/ml hydrocortisone, 50 U/ml penicillin and 50 μg/ml streptomycin) were resuspended at a concentration of $10^5$ cells per 4.0 ml. Eight-chambered RS glass slides (Nalgene) were coated with 35 μl Matrigel per well and left to solidify for 15 min. The cells were mixed 1:1 with assay medium containing 4% Matrigel and 10 ng/ml EGF, and 400 μl were added to each chamber of the Matrigel-coated eight-chambered slide. Assay medium containing SFLLRNPNDK PAR$_1$ activation peptide (SEQ ID NO: 52) and 5 ng/ml EGF was replaced every 4 days. The images were taken between days 8-12. In the representative experiment shown images were taken on day 10. The media and supplements were replaced every 4 days and thus, the activating peptide was added fresh to the medium every 4 days.

Example 2

The Cytoplasmic Tail of PAR1 is Involved in Tumor Promotion Via Binding of Etk/Bmx PAR$_1$-Enhanced Tumor Growth and Angiogenesis In Vivo is Abrogated in the Presence of a Truncated PAR$_1$ Form.

To investigate the role of PAR$_1$ signaling in breast tumor growth and vascularization in vivo, wt hPar1 and deletion constructs [e.g., L369Z, which lacks the entire cytoplasmic tail, and Y397Z, which exhibits persistent signaling due to impaired internalization (Shapiro M J, et al (1996) *J. Biol. Chem.* 271: 32874-32880; Hammes S R, and Coughlin S R (1999) Biochemistry 38: 2486-2493)] (FIG. 2A) were over-expressed in MCF7 cells. RT-PCR analysis of the cells transfected with wt hPar1, Y397Z hPar1, truncated hPar1 or empty vector was performed as described above using primers to PAR$_1$ N-terminus, C-terminus, or GAPDH. As can be seen in FIG. 2B the transfected cells (except for the empty vector) expressed N-terminus PAR1. As expected, only the cells that were transfected with wt hPar1 expressed the c-tail portion of PAR1. The functional outcome of MCF7 cells over-expressing various hPar1 constructs in vivo was assessed by analyzing orthotopic mammary fat pad tumor development. MCF7 cells over-expressing either Y397Z or wt hPar1 constructs (e.g., MCF7/Y397Z hPar1; MCF7/wt hPar1) markedly enhanced tumor growth in vivo following implantation into the mammary glands (FIGS. 2C and 2D), whereas MCF7 cells over-expressing truncated hPar1 behaved similar to control MCF7 cells in vector-injected mice, which developed only very small tumors (FIG. 2C). The tumors obtained with MCF7/wt hPar1 and MCF7/Y397Z hPar1 were 5 and 5.8 times larger, respectively, than tumors produced by the MCF7/empty vector-transfected cells. Histological examination (H&E staining) showed that while both MCF7/wt hPar1 and MCF7/Y397Z hPar1 tumors infiltrated into the fat pad tissues of the breast, the MCF7/Y397Z hPar1 tumors further infiltrated the abdominal muscle (FIG. 2D). In contrast, tumors produced by empty vector or truncated hPar1-transfected cells were capsulated, with no obvious cell invasion. In addition, the Y397Z hPar1 and wt hPar1 constructs exhibited intense vascularization and appeared reddish as opposed to the pale appearance of tumors generated by either empty vector or truncated hPar1.

Proliferation levels were evaluated by immunostaining with Ki-67 and were 3 times higher in Y397Z hPar1 or wt hPar1 tumors (FIG. 3) than in the small tumors produced by either empty vector or truncated hPar1-transfected cells ($p<0.0001$, FIG. 3B). Tumor growth can also be attributed to blood vessel formation (Griffin C T, et al (2001) *Science* 293: 1666-1670; Connolly A J, et al (1996) *Nature* 381: 516-519). The hPar1-induced breast tumor vascularization was assessed by immunostaining with anti-lectin- and anti-CD31 antibodies. Both MCF7/Y397Z and MCF7/wt hPar1 tumors were intensely stained (FIGS. 3A, 3C and 3D). In contrast, only a few blood vessels were found in the small tumors of empty vector or truncated hPar1 (FIGS. 3A, 3C and 3D). Thus, both MCF7/wt hPar1 and MCF7/Y397Z hPar1 cells were shown to effectively induce breast tumor growth, proliferation and angiogenesis, while the MCF7/truncated hPar1 and MCF7/empty vector-expressing cells had no significant effect. Histological evaluation and scoring was performed as described above.

PAR$_1$ C-Tail Binds the she Adaptor Protein.

Figure 4:
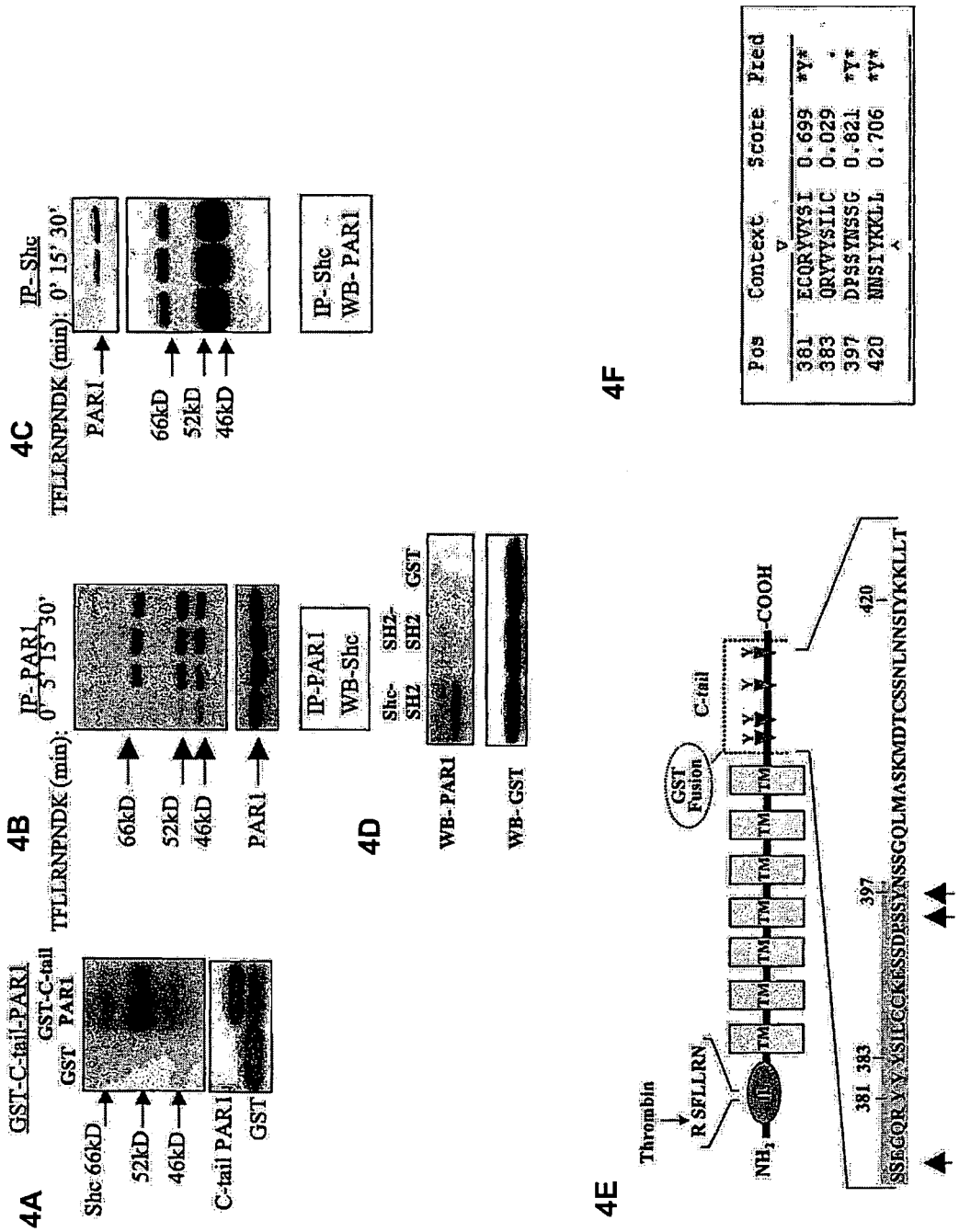
FIG. 4A shows Western blot analysis performed using anti-Shc antibodies, demonstrating binding of $PAR_1$ GST-C-tail to Shc adaptor.
FIGS. 4B and 4C show co-immunoprecipitation analyses of $PAR_1$ and Shc. Lysates of non-activated or TFLLRNPNDK (SEQ ID NO: 35)-activated MDA-MB-435 cells were co-immunoprecipitated with either anti-$PAR_1$ (4B) or anti-Shc (4C) antibodies.
FIG. 4D shows $PAR_1$ binding to the Shc-SH2 domain. MDA-MB-435 cell lysates were loaded onto columns of GST-Shc-SH2, GST linked to a tandem SH2 from a non-relevant protein, or GST alone. Specifically-bound proteins were eluted and detected with anti-$PAR_1$ antibodies.
FIG. 4E is a schematic representation of the structure of $PAR_1$-C-tail. IL—internal ligand (RSFLLRN (SEQ ID NO: 55)); TM—transmembrane (SSECQRYVYSILCCKESSDPSYNSSGQLMASK-MDTCSSNLNNSIYKKLLT (SEQ ID NO: 56)). Important tyrosine (Y) residues are indicated and the conserved sequence is highlighted.
FIG. 4F is a table showing analysis of $PAR_1$ C-tail Y-residues by NetPhos 2.0 server. $Y_{381}$ (SEQ ID NO: 57), $Y_{397}$ (SEQ ID NO: 59) and $Y_{420}$ (SEQ ID NO: 60) were scored highly likely to undergo phosphorylation, as shown in the table. "Pied" means "prediction" for the predicted score of each of the Y tyrosine residues that is relevant to phosphorylation. The $Y_{383}$ sequence is (SEQ ID NO: 58).

To identify proteins that associate with the PAR$_1$ C-terminus and participate in the tumor signaling pathway, the cytoplasmic tail of hPar1 was fused to a GST protein and used as "bait" to specifically detect associated proteins. Lysates obtained from a highly metastatic breast carcinoma line (e.g., MDA-MB-435 cells) were assessed for binding to the GST-PAR$_1$ C-tail column. After an adequate binding period of the designated cell lysates to the columns, a washing step was performed. This step was performed in order to wash out all non-specific proteins, leaving the GST-PAR$_1$-C-tail column firmly bound to targeted cell lysate proteins. Next, specifically-bound proteins were eluted via the addition of gel "sample buffer" and detected by Western blot analysis using anti-Shc antibodies. Amino acid sequence analysis of proteins bound to the column repeatedly indicated the presence of the Shc adapter protein. Indeed, application of MDA-MB-435 cell lysates onto a GST PAR$_1$ C-tail column or a GST control column showed the three Shc isoforms specifically bound to the GST-PAR$_1$-C-tail column, but not to the GST control column (FIG. 4A). Shc isoforms refer to a series of proteins (e.g., 66, 52 and 46 kDa) termed Shc (Src homology 2/$\alpha$-collagen-related) (Pelicci G, et al. (1992) *Cell* 70: 93-104: Pronk G J, et al (1993) *J Biol. Chem.* 268: 5748-5753). cDNA analyses of the family proteins has demonstrated that the 46- and 52-kDa species arise from alternative translation initiation sites within the same transcript, giving rise to a 59-amino acid terminal truncation of the 46-kDa isoform compared to the 52-kDa isoform. In contrast, the 66-kDa species most likely arises from an alternatively spliced message since there is only one Shc gene and the carboxy terminal antibodies cross react with all three molecular weight species. Co-immunoprecipitation studies using either PAR$_1$ (FIG. 4B) or Shc antibodies (FIG. 4C) confirmed the PAR$_1$-Shc association 5 min after TFLLRNPNDK activation; this association remained high during the 30 min of analysis (FIGS. 4B and C). The Shc protein comprises multiple protein docking sites, including SH2, phospho-tyrosine binding site (PTB) and collagen homology domains 1 and 2 (CH1, CH2). When a GST-Shc-SH2 domain pull-down assay was used following loading with PAR$_1$ activated MDA-MB-435 cell lysates, PAR$_1$-specific binding to the Shc-SH2 domain was obtained. In contrast, when the tandem SH2 domain from an irrelevant protein was used as a control, no binding of PAR$_1$ was observed (FIG. 4D). Using the NetPhos 2.0 server four candidates: $Y_{381}$, $Y_{383}$, $Y_{397}$, $Y_{420}$ (FIGS. 4E and 4F) were identified as PAR$_1$ C-tail putative tyrosine residues capable of serving as possible binding sites for the Shc protein. Of these, only three were predicted to undergo phosphorylation: $Y_{381}$, $Y_{397}$ and $Y_{420}$ (FIG. 4F). Since, as shown above, Y397Z hPar1 was potent in signaling (FIGS. 2 and 3), it was postulated that the Shc binding site(s) in the PAR$_1$ C-tail is/are located upstream of tyrosine 397. Indeed, sequence alignment of PAR$_1$ C-tail in nine different species demonstrates several highly conserved regions (data not shown), among which are the $Y_{381}VY_{383}$ residues. Replacement of the relevant tyrosine (Y) residues upstream to Y397Z hPar1 with alanine (Ala, A) (e.g., $Y_{381}A$ or $Y_{383}A$ and the double mutant $Y_{381}A$ & $Y_{383}A$) did not prevent the recruitment and physical association between Shc and PAR$_1$ (see FIG. 9A).

$Y_{381}A$-hPar1 Exhibits High Metastatic Potential.

Figure 5:
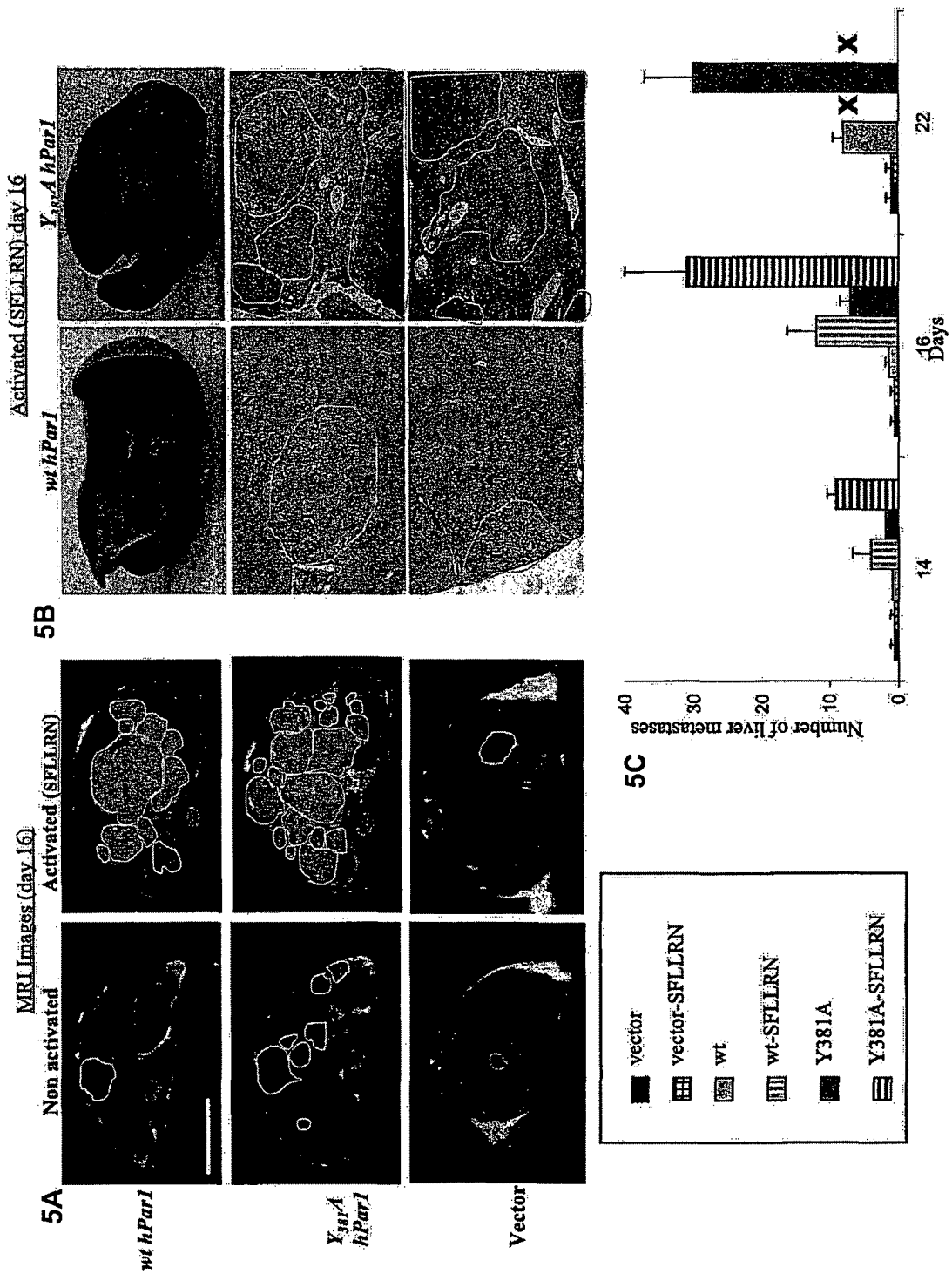
FIG. 5A shows MRI analysis of tumors induced by injection of mouse CT-26 colon carcinoma cells over-expressing wt hPar1, $Y_{381}A$ hPar1 or empty vector constructs. Tumor assessment was performed using $T_2W$ fast SE images (TR/TE=2000/40 ms). Representative axial liver sections of wt hPar1 or $Y_{381}A$ hPar1 CT-26-transfected cells, obtained at day 16, in the absence (left panel) or presence (right panel) of SFLLRN, are seen. Liver margins are marked with a dashed line; lines mark tumor foci; scale bar represents a size of 1 cm and applies to all the images in A.
FIG. 5B shows anatomical and histological examination of the tumors. Gross anatomical photos (Top) and H&E staining of liver sections (harvested on day 16) of activated wt hPar1 or $Y_{381}A$ hPar1 CT-26 cells (mid and lower panels). Lines mark tumor foci; original magnification ×100.
FIG. 5C is a histogram of the number of liver metastases per mouse as measured by MRI. The experiments were performed in the presence or absence of the $PAR_1$ agonist peptide (n=3-5 mice/group). X stands for sacrificed mice with overloaded liver tumors.

The functionality of the $Y_{381}A$ hPar1 mutant was further demonstrated in vivo using a colorectal-liver metastasis model (Qiu Y, et al (1998) *Proc Natl Acad Sci USA* 95: 3644-3649), which provides a rapid metastatic model of liver foci formation. Mouse CT-26 colon carcinoma cells (that do not express endogenous hPar1) were genetically engineered to over-express wt hPar1, $Y_{381}A$ hPar1 or empty vector constructs. These over-expressing cells were injected intra-splenically into CB6F1 mice (either PAR$_1$-activated or not) to generate liver metastases. Tumor growth kinetics and liver metastatic foci appearance were monitored twice a week by MRI. Both wt hPar1 and Y$_{381}$A hPar1 enhanced liver metastatic foci formation, compared to control CT-26 cells. Furthermore, mice inoculated with cells expressing Y$_{381}$A hPar1 showed especially extensive and rapid appearance of liver metastasis as compared to mice inoculated with cells over-expressing wt hPar1 (FIG. 5). Representative MRI images (FIG. 5A) of excised livers and histological sections (FIG. 5B), obtained on day 16, demonstrated high metastatic potential of both activated Y$_{381}$A hPar1 and wt hPar1. An elevated number of metastatic foci were observed with the wt hPar1 after PAR$_1$ activation (FIG. 5A), and an even more dramatic increase was obtained with the activated Y$_{381}$A hPar1 construct (FIGS. 5A, C). Quantification of liver metastasis as a function of time is shown in FIG. 5C. These results emphasized that the Y$_{381}$A hPar1 mutated construct is at least as functional as the wt hPar1, and the substitution of Y to A did not impair the ability of hPar1 to initiate signaling and therefore result in metastasis. The results may further suggest that Shc does not bind directly to PAR$_1$ C-tail, since replacement of a key tyrosine residue by alanine (Y381A) does not impair PAR$_1$ function as manifested by metastatic foci formation. It is thus postulated that whereas Shc is not associated with PAR1 via the traditional tyrosine-phosphorylated-SH2 complex formation, it probably involves a third mediator connecting with PAR$_1$. The molecular mechanism of Y$_{381}$A hPar1-enhanced liver metastasis remains to be fully elucidated.

Antibody-Array for Protein-Protein Interactions Reveals Signaling Candidates.

To detect the putative mediator(s) linking PAR1 to potential signaling proteins, custom-made antibody-array membranes were examined. Aggressive breast carcinoma MDA-MB-435 cells (with high hPar1 levels) were incubated with the antibody-array membranes before and after PAR$_1$ activation (15 minutes). Several activation-dependent proteins which interact with PAR$_1$ were identified, including ICAM, c-Yes, Shc and Etk/Bmx (FIG. 1).

Figure 6:
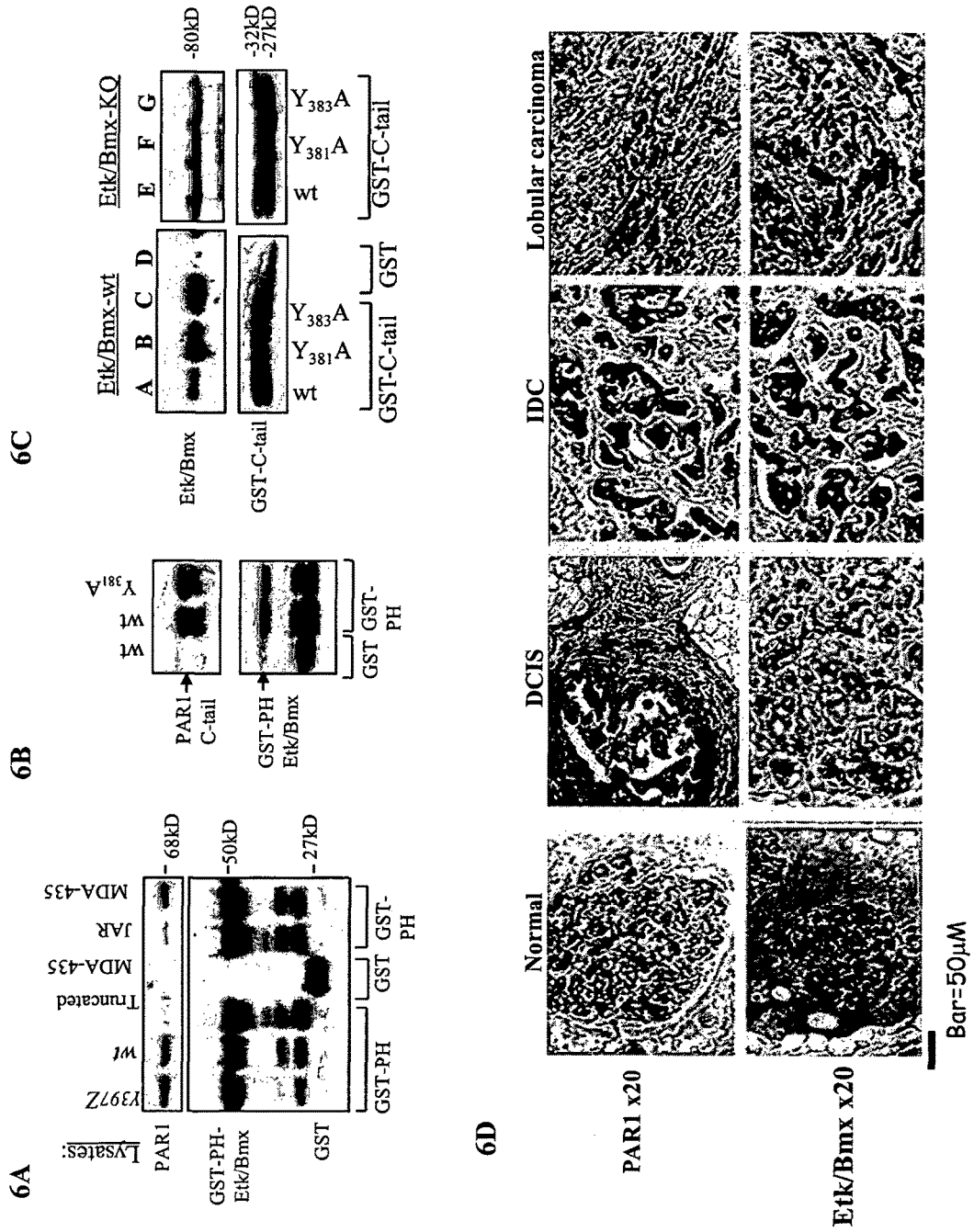
FIG. 6A is a gel demonstrating association between $PAR_1$ and Etk-PH domain. Lysates of cells over-expressing Y397Z, wt or truncated hPar1, as well as a lysate of cells that do not express $PAR_1$ (e.g., JAR) and a lysate of cells that express high levels of $PAR_1$ (e.g. the highly metastatic MDA-435 cells) were applied to a GST-Etk-PH column. Specifically-bound proteins were detected using anti-$PAR_1$ antibodies.
FIG. 6B is a gel demonstrating binding of Etk-PH domain with purified $PAR_1$ C-tail. $PAR_1$ C-tail was cleaved from the immobilized GST-C-tail, purified and re-applied onto a GST-Etk-PH domain column.
FIG. 6C is a gel demonstrating binding of GST-$PAR_1$ C-tail of wt and mutants. Lysates of HEK293 cells transfected with either Etk/Bmx (A-D) or kinase-inactive Etk/Bmx (KQ; E-G), were applied on various GST-$PAR_1$-C-tail columns ($PAR_1$-C-tail of wt, $Y_{381}A$, $Y_{383}A$) or GST-control column. Specifically-bound proteins were identified using anti-Etk/Bmx antibodies. Levels of GST were used as a control for protein loading.
FIG. 6D is a photograph demonstrating immunohistological staining of $PAR_1$ and Etk/Bmx on breast tissue biopsy specimens. Antibodies directed against $PAR_1$ (upper panel) or Etk/Bmx (lower panel) were applied to normal and cancerous breast tissue specimens. The cancerous tissues include DCIS (ductal carcinoma in situ), IDC (invasive ductal carcinoma) and lobular invasive carcinoma (lobular carcinoma).

Etk/Bmx-PAR1 interactions were characterized by binding lysates exhibiting various hPar1 forms to GST-Etk/Bmx. wt hPar1 and Y$_{381}$A hPar1 purified C-tails (FIG. 6B). Next, various modified PAR$_1$-GST-C tail constructs (e.g., wt hPar1, Y$_{381}$A hPar1 and Y$_{383}$A hPar1) were analyzed for binding to either wt- or kinase-inactive Etk/Bmx (KQ) cell lysates. A tight association between the PAR$_1$ C-tail and Etk/Bmx was obtained, independent of whether wt hPar1 or the Y/A mutant forms of PAR$_1$ C-tail were examined. This was demonstrated for both wt- and KQ-Etk mutant (FIG. 6C).

Differential Expression of Etk/Bmx in Breast Biopsies

PAR$_1$ is known to be highly expressed in breast carcinoma specimens, but not in normal breast tissue. Immunohistochemical staining of PAR$_1$ tissue sections confirms the earlier described RNA riboprobe analysis for hPar1. Invasive carcinoma specimens were selected from infiltrating ductal carcinoma (IDC) of high nuclear grade and with evidence of vascular invasion and lymph node metastases. Immunohistological analyses of both PAR$_1$ and Etk/Bmx showed little staining in comedo DCIS and ductal carcinoma in situ, but high levels of staining in IDC and lobular carcinoma (FIG. 6D).

The combined histological results are shown in Table 1. The results were assessed and scored as outlined in the Materials & Method section. The measurements per slide section were carried out using anatomical compartments, using an ocular micrometer (WHIOX2, Olympus, N.J., USA).

The microscope was calibrated with a micrometer slide before each measurement. On examining the sections for selection of fields tumor cells from the most cellular area at the center of the tumor were selected. Necrotic and inflammatory areas were avoided. Eight microscopic fields were screened. Ten cells per each field were selected and no less than 50 cells/tumor case were assessed. The positive rate of staining is expressed as a mean±SD per tumor histological subtype from selected cases. Specific staining is observed in both PAR$_1$ and Etk/Bmx, with particularly strong staining seen in IDC and lobular carcinoma. No staining is seen in the normal breast tissue.

This staining represents a total of 36 cases as outlined for each histological subtype in Table 1, performed three times per category.

TABLE 1

Expression of PAR$_1$ and Etk/Bmx in breast cancer biopsy specimens

| Histological subtype | Cases (N = 36) | Positive cells Mean ± SD | | +1 | | +2 | | +3 | |
|---|---|---|---|---|---|---|---|---|---|
| | | PAR$_1$ | Etk/Bmx | PAR$_1$ | Etk/Bmx | PAR$_1$ | Etk/Bmx | PAR$_1$ | Etk/Bmx |
| Normal | 12 | 0.8 ± 0.2 | 1.2 ± 0.2 | 0 | 1 | 0 | 0 | 0 | 0 |
| DCIS | 8 | 12.5 ± 3.7 | 14 ± 3.0 | 2(25%) | 1(12.5%) | 6(75%) | 7(87.5%) | — | — |
| IDC | 9 | 40 ± 10.5 | 42 ± 12.3 | 2(22%) | 1(11%) | 1(11%) | 0 | 5(55%) | 6(66%) |
| Lobular carcinoma | 7 | 45 ± 7.3 | 43 ± 11.6 | 1(14%) | 0 | 1(14%) | 1(14%) | 6(85%) | 5(71.4%) |

Histological scoring of (N) cases: +1 less than 25% positive cells (weak positive); +2 between 25-75% positive cells (moderate); +3 more than 75% of positive cells (strong). All controls were negative (0-5% positive cells). Extent of expression classified by score (1-3), number of positive cells/field (x = 8).

While Y397Z hPar1 and wt hPar1 showed specific association with Etk/Bmx, lysates of truncated hPar1 or JAR cells (lacking PAR$_1$) exhibited no binding (FIG. 6A). In order to substantiate the physical association between PAR$_1$ C-tail and Etk/Bmx-PH domain the C-tail portion of both wt- and Y381A hPar1-modified tail were proteolytically cleaved and the purified fragments were applied onto a GST-PH Etk/Bmx column. Specific binding was observed with both the These results further suggest a direct correlation between PAR$_1$ and Etk/Bmx expression in malignant breast cancer progression.

Hierarchy of Binding

Next, the chain of events mediating the signaling of PAR$_1$ C-tail-Shc and Etk/Bmx was determined. MCF7 cells that express little or no hPar1 were ectopically forced to over-express hPar1. When co-immunoprecipitation with anti- PAR₁ antibodies following PAR₁ activation was performed, surprisingly, no Shc was detected in the PAR₁ immunocomplex (FIG. 7A; MCF7/hPar1; right panel). Shc association with PAR₁ was fully rescued when MCF7 cells were initially co-transfected with Etk/Bmx (FIG. 7A), with abundant assembly of Shc in the immunocomplex. Thus, Etk/Bmx is a critical component that binds to activated PAR₁ C-tail and enables subsequent binding of Shc. Shc may bind either to phosphorylated Etk/Bmx, via the SH2 domain, or in an unknown manner to the PAR₁ C-tail, provided that Etk/Bmx is present and is PAR₁-bound. One cannot, however, exclude the possibility that Bmx binds first to Shc and only then does the complex of Etk/Bmx-Shc bind to PAR-1.

Identification of PAR₁-Etk/Bmx Binding Region: Functional Consequences.

Figure 7:
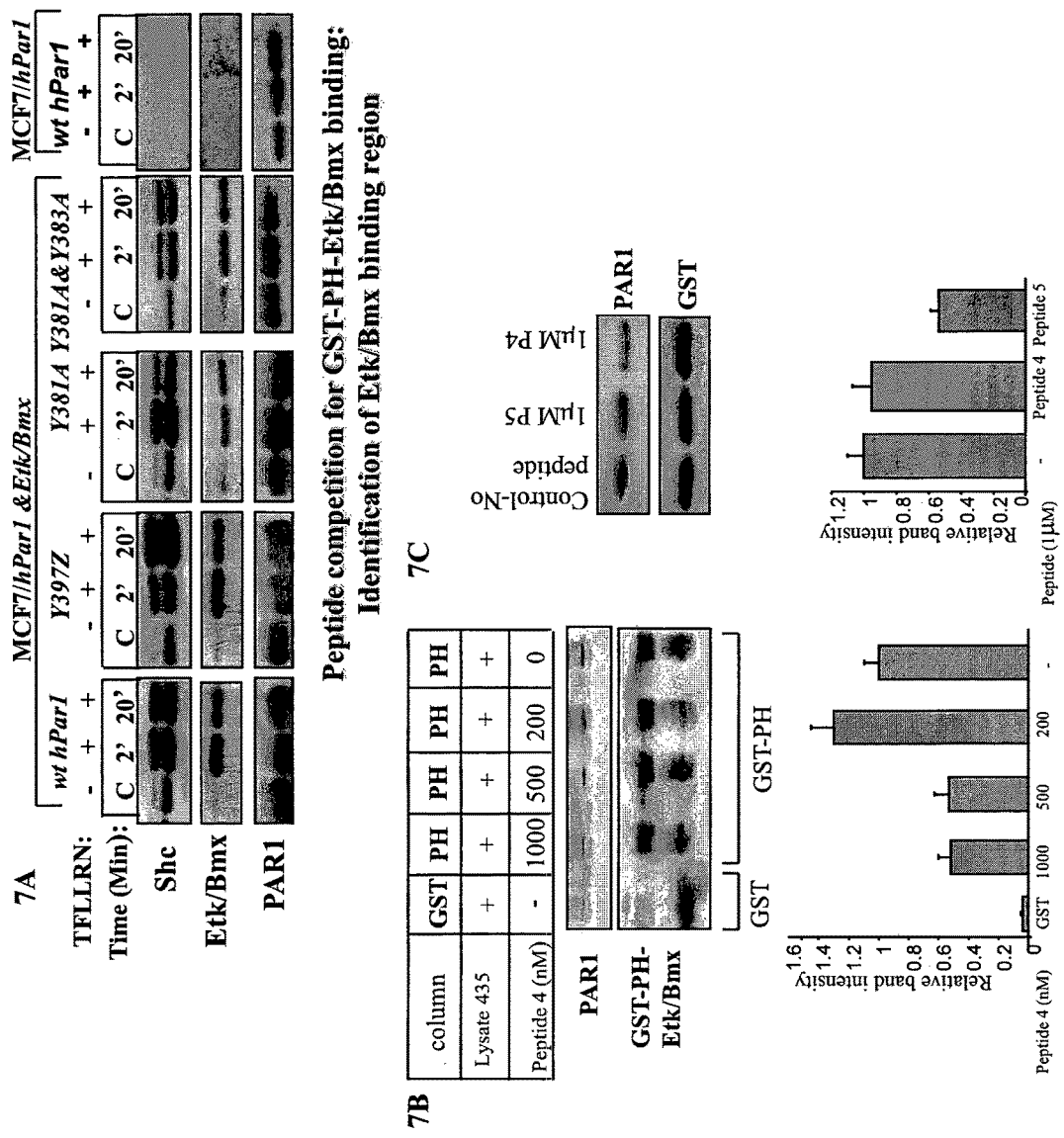
FIG. 7A is a gel demonstrating binding reactions between Etk/Bmx, Shc and PAR1 C-tail as demonstrated by immunoprecipitation (IP). The IP was performed using anti-PAR1 (ATAP, Santa Cruz, Calif.).
FIGS. 7B and 7C are photographs of gels showing peptide competition for PAR1 binding to GST-PH-Etk/Bmx. In the lower panel, a representative histogram shows the relative intensities of the bands expressed as a ratio of PAR1 to GST-PH.

Peptides (representing various regions in PAR₁ C-tail) were used in a competition analysis assay for the binding of PAR₁ cell lysates to GST-PH-Etk/Bmx. An 18-amino-acid peptide encompassing residues 375-392 of PAR₁ C-tail (termed peptide 4) yielded a dose-dependent inhibition within the range of 1-1000 nM applied peptide (FIG. 7B). Two other peptides, representing PAR₁ C-tail 387-400 (FIG. 7C; termed peptide 5) or residues 393-412 did not compete.

Figure 8:
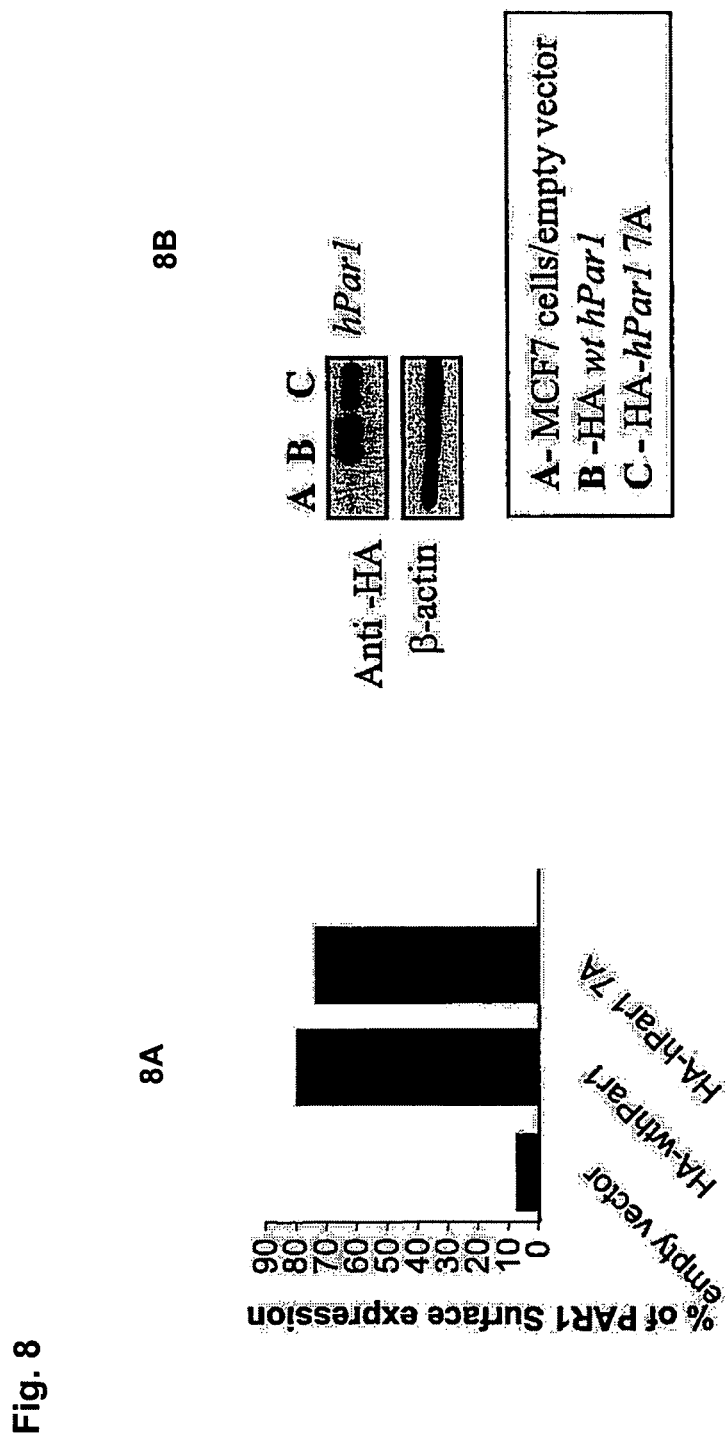
FIG. 8A is a histogram demonstrating the percentage of PAR1 surface expression in cells transfected with empty vector, HA-wthPar1 and HA-hPar1 7A.
FIG. 8B is a gel demonstrating staining with anti HA antibodies.
Figure 9:
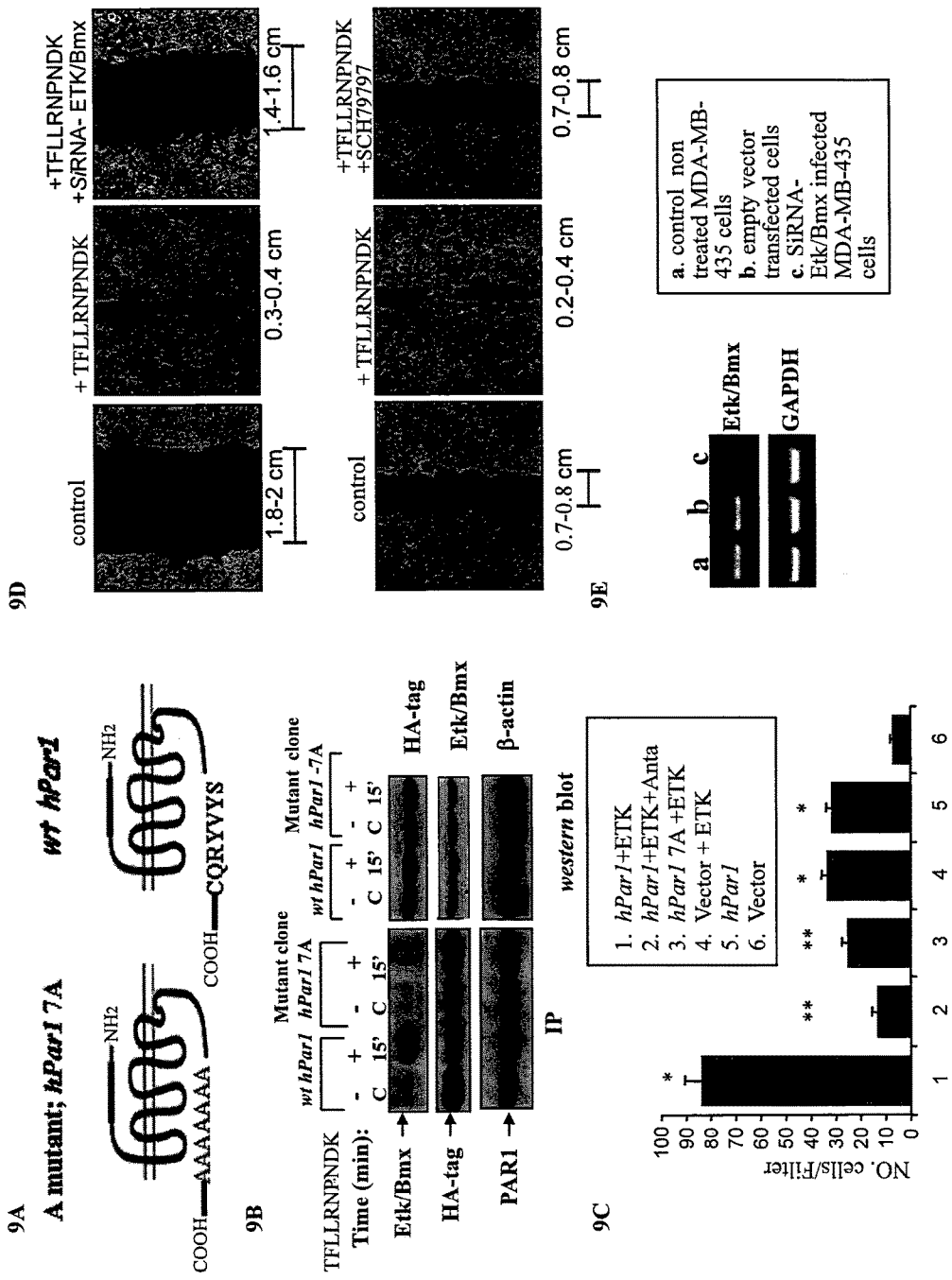
FIG. 9A is a schematic representation of wt hPar1 and the mutant hPar1-7A.
FIG. 9B is a gel showing immunoprecipitation (IP) of $PAR_1$ with Etk/Bmx after activation in stable clones expressing either HA-tagged wt hPar1 and/or a mutant construct of HA-hPar1-7A. The IP was carried out using anti-HA antibodies. The Western blots were subjected to anti-Bmx for the identification of Etk/Bmx-associated $PAR_1$. Levels of the HA-tag (for $PAR_1$) are shown in the middle panel. Similarly, levels of $PAR_1$ are also shown by application of anti-$PAR_1$ (lower panel). The right section shows levels of plasmid transfection efficiencies in the cells, as indicated by HA-$PAR_1$ and Etk/Bmx analysis by Western blots.
FIG. 9C is a histogram showing numbers of invading cells (mean±SD) of ten fields per filter in a Matrigel invasion assay. These data are representative of three experiments.
FIG. 9D is a photograph showing MDA-MB-435 cell monolayer scratched to introduce an equal gap-area. Control: control untreated cells; TFLLRNPNDK-activated or SiRNA-Etk/Bmx and TFLLRNPNDK-activated.
FIG. 9E is a gel showing RT-PCR analysis of the level of Etk/Bmx in MDA-MB-435 cells before and after SiRNA-Etk/Bmx cell infection.

Based on the competition assay mutated hPar1 constructs with successive replacement of seven residues (378-384; CQRYVYS) were prepared. MCF7 clones expressing either HA-hPar1-7A or HA-wt hPar1 were prepared. As shown in FIG. 8 the transfected clones properly expressed HA-PAR1. FIG. 9A shows a schematic representation of wt hPar1 and the mutant hPar1-7A. The clones expressing either HA-tagged wt hPar1 or a mutant construct of HA-hPar1-7A were activated and further analyzed for co-immunoprecipitation (IP) of PAR₁ with Etk/Bmx. The IP was carried out using anti-HA (sc-7392; Santa Cruz, Calif.). The blots were detected by anti-Bmx (Transduction Laboratories, BD Biosciences, CA) for the identification of Etk/Bmx-associated PAR₁. As shown in FIG. 9B ectopic expression of the hPar1-7A mutant construct abrogated binding of Etk/Bmx to PAR₁ C-tail. We thus conclude that the critical region for Etk/Bmx binding to PAR₁ C-tail resides in the vicinity of CQRYVYS. Levels of the HA-tag (for PAR₁) are shown in the middle panel of FIG. 9B. Similarly, levels of PAR₁ are also shown by application of anti-PAR₁ (ATAP; Santa Cruz, Calif.) (lower panel). The right section shows levels of plasmid transfection efficiencies in the cells, as indicated by HA-PAR₁ and Etk/Bmx analysis by western blots. As seen, only the wt hPar1 co-immunoprecipitated with Etk/Bmx (wt hPar1), while the mutant HA-hPar1-7A clone (mutant clone hPar1-7A) failed to co-immunoprecipitate. This takes place under conditions whereby both constructs are well expressed, as evidenced by anti-HA-antibodies (western blot; right panel).

MCF7 cells stably expressing HA-wt-hPar1 and Etk/Bmx, or HA-hPar1-7A mutant and Etk/Bmx were examined in a Matrigel invasion assay. Invading cells were counted and the mean±SD of ten fields per filter was determined. Stable HA wt hPar1 clone or HA-hPar1-7A mutant clone were co-transfected with Etk/Bmx construct and TFLLRN-PNDK-activated. Marked Matrigel invasion is seen in the wt hPar1 and Etk/Bmx clones (FIG. 9C). Low invasion levels are observed in the presence of hPar1-7A mutant and Etk/Bmx, hPar1 alone, empty vector, vector and Etk/Bmx or PAR₁ antagonist. These data are representative of three experiments.

In a parallel experiment, a wound assay for determining the rate of cell migration, showing the ability of the cells to fill in gaps in an MDA-MB-435 cell monolayer, was performed. MDA-MB-435 cell monolayer expressing endogenous Etk/Bmx was scratched to introduce an equal gap-area under the following conditions: control untreated cells, TFLLRNPNDK-activated or SiRNA-Etk/Bmx and TFLL-RNPNDK-activated. Rapid closure of the wound was obtained 24 hours under PAR₁ activation as compared to control untreated cells. In contrast, no migration and closure of the wound was seen when the endogenous Etk/Bmx level of the cells was knocked down using an siRNA-Etk/Bmx construct (FIG. 9D, top panel) and they were TFLLRN-PNDK-activated. In another set of wound experiments, attenuated wound closure was seen in the presence of the V antagonist SCH79797 and SFLLR NPNDK PAR₁ activation for 24 h, similar to the control untreated cells. These data are representative of four experiments. Similar inhibition was obtained in the presence of the PAR₁ antagonist, SCH 79797 (FIG. 9D, bottom panel), pointing to the important role of both PAR₁ and Etk/Bmx in wound closure/migration of PAR₁-activated MDA-MB-435 cells.

FIG. 9E shows results of RT-PCR analysis showing the level of Etk/Bmx in MDA-MB-435 cells before and after SiRNA-Etk/Bmx cell infection.

Figure 10:
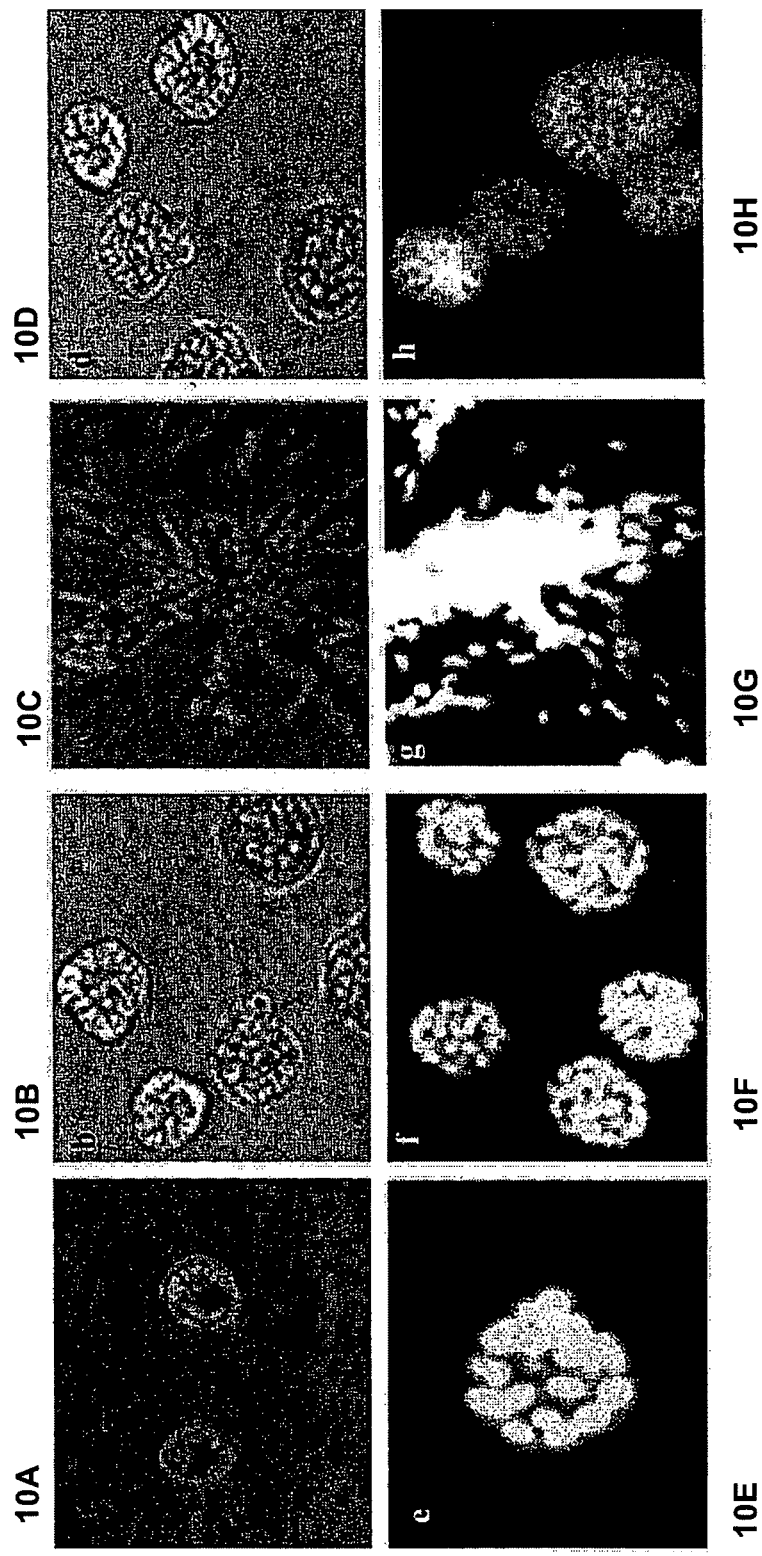
FIG. 10A-H are photographs showing morphogenesis of MCF10A spheroids infected with either wt hPar1, mutant hPar1-7A or with Etk/Bmx, maintained in 3-D Matrigel cultures. Fig. A-D show representative phase-contrast microscopic images of MCF10A cells under the following conditions: A. control untreated MCF10A. B. MCF10A cells infected with Etk/Bmx and SFLLRNPNDK $PAR_1$-activated. C. MCF10A cells infected with both wt hPar1 and Etk/Bmx and SFLLRNPNDK-activated. D. MCF10A cells infected with both mutant hPar1-7A and Etk/Bmx and SFLLRN-PNDK-activated. Fig. E-H show representative confocal microscopic images of MCF10A acini: E. Control untreated MCF10A, DAPI stained nuclei in a representative spheroid. F. MCF10A cells infected with both the mutant hPar1-7A and Etk/Bmx and SFLLRNPNDK-activated; DAPI staining of spheroid nuclei. G. MCF10A cells infected with both the wt hPar1 and Etk/Bmx and SFLLRNPNDK-activated; DAPI staining of the nuclei. H. MCF10A cells infected with both the mutant hPar1-7A and Etk/Bmx and SFLLRN-PNDK-activated, stained for cell-cell contact with anti-E-cadherin.

The highly ordered tissue organization of normal epithelia is aggressively disrupted in pathological conditions. This is well recapitulated in the MCF10A cell-growth model, mimicking epithelia apico-basal polarity (Desgrosellier J S, et al. (2009) *Nat Med* 15: 1163-1169). The morphogenesis of MCF10A mammary acini in three-dimensional (3-D) basement membrane cultures was examined. Normal-appearing intact spheroids are formed in the presence of control Etk/Bmx-expressing MCF10A cells and activation by SFLLRNPNDK, a PAR₁ agonist peptide (FIG. 10A; a, b). In contrast, in the presence of ectopically forced hPar1 (expressing also Etk/Bmx) and following PAR₁ activation, an oncogene-like, migratory morphogenesis was obtained which was characterized by a complete loss of the cell-cell tight junction contacts and the invaded basement membrane architecture (FIG. 10A; c and g). Significantly, when the MCF10A cells (in the presence of endogenously expressed Etk/Bmx) were infected with the mutant cytoplasmic form of hPar1 (hPar1-7A) and SFLLRNPNDK PAR₁-activated, nearly normal-appearing spheroid morphology was obtained (FIG. 10A; d, f). This outcome highlights the fact that by preventing immobilization of Etk/Bmx on PAR₁ C-tail, inhibition of invasion and lack of apico-basal polarity morphogenesis of an oncogene-like phenotype in MCF10A cells are observed.

Analyses of hPAR1 7A Mutants in the Xenograft Animal Model

Figure 11:
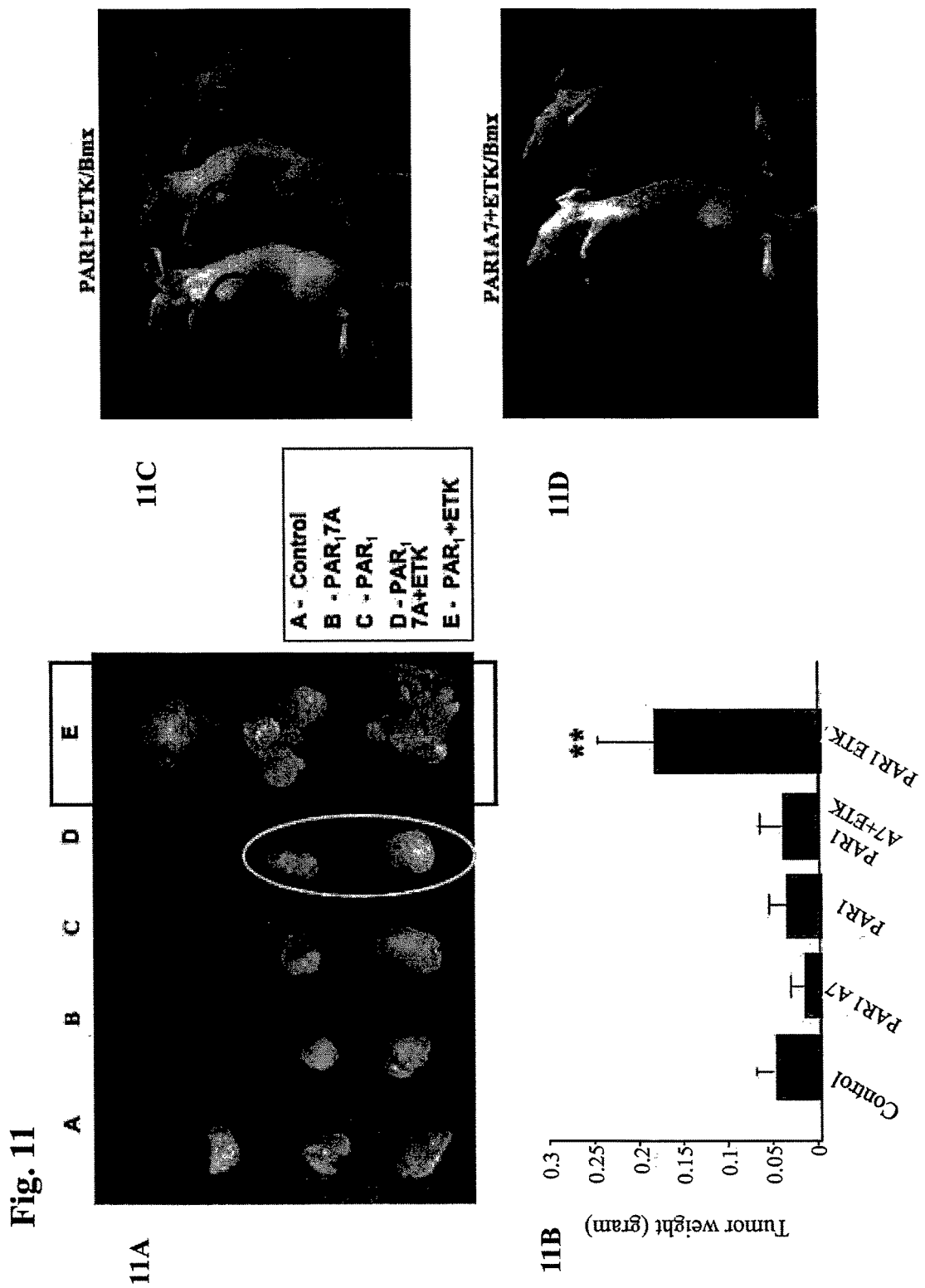
FIG. 11A is a photograph showing tumors generated by cells transfected with various constructs.
FIG. 11B is a histogram showing tumor weight.
FIGS. 11C and 11D are photographs showing mice having tumors generated by cells transfected with PAR1+Etk/Bmx (C) or PAR1A7+Etk/Bmx (D).

In vivo experiments were performed with hPAR1 7A mutants in the mammary gland xenograft model describe above. Stable MCF-7 clones were generated. These clones expressed: wt hPar1 or hPar1 7A mutant in the presence or absence of Etk/Bmx. As described above, these clones were further analyzed in vivo in the xenograft animal model. The mice were pre implanted prior to injection with 17-β-estradiol pellets. Next the clones were orthotopically injected to the mice mammary glands. Enormously large tumors were generated in mice injected with cells expressing hPar1-Etk/Bmx. The experiment was stopped at an early stage (e.g., 20 days post injection) due to heavy tumor burden. In-contrast, very small tumors, similar to the empty vector injected cells were generated in the presence of hPar1-7A mutant, incapable of binding Etk/Bmx. Thus, as shown above for the MCF7/Y397Z hPar1 cells, it is demonstrated that when hPar1 is unable to bind Etk/Bmx, very small to no tumors are generated (FIG. 11). Tumor weight is shown by the histograms (FIG. 11B).

Immunohistological Evaluation of the Tumor Sections

Figure 12:
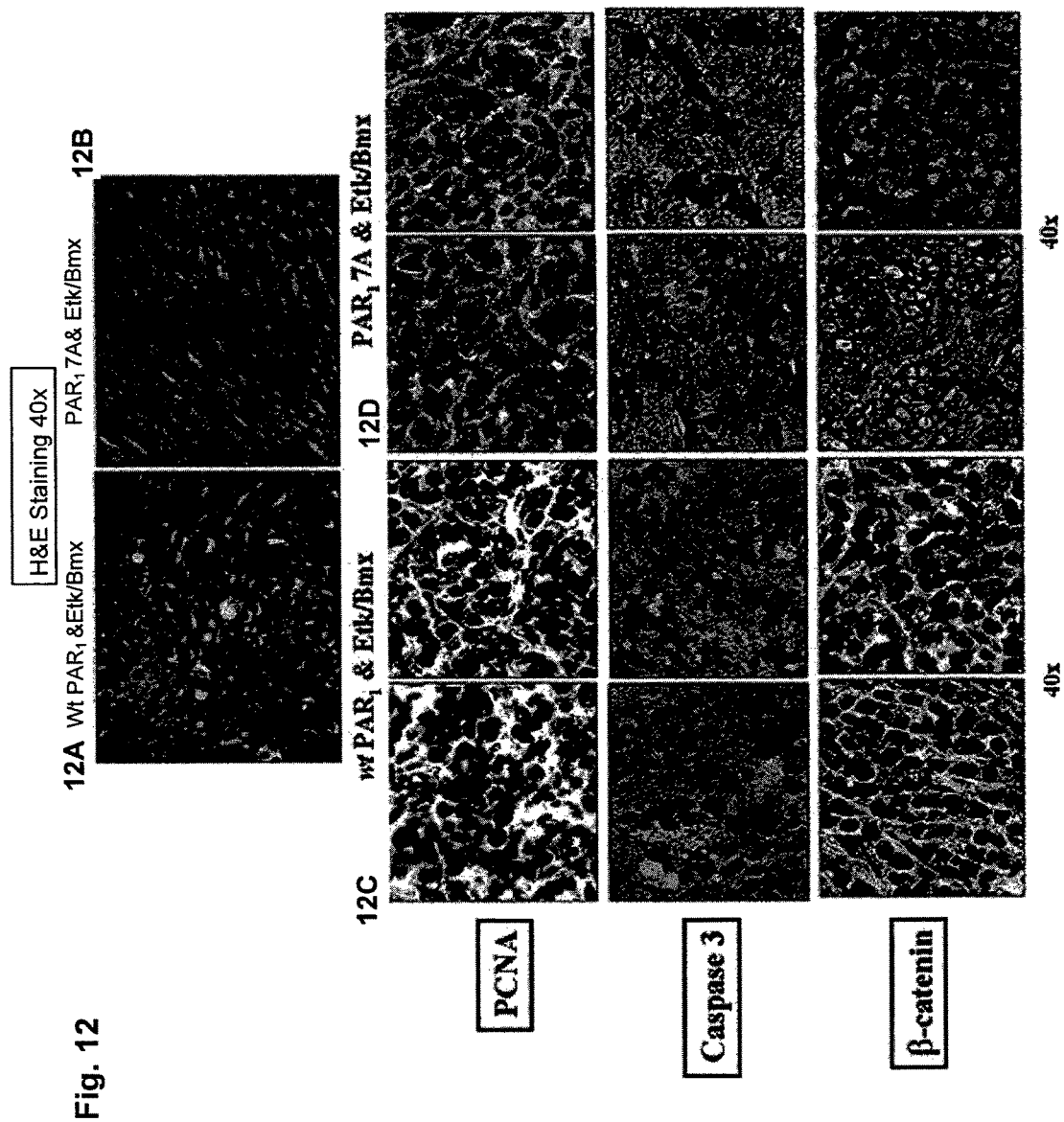
FIGS. 12A and 12B are photographs showing histological examination of a tumor section (hematoxylin eosine staining).
FIGS. 12C and 12D are photographs of tissue sections of tumors produced by cells transfected with wtPAR1 & Etk/Bmx (12C) and tumors produced by cells transfected with PAR1 7A & Etk/Bmx (12D), stained with anti PCNA antibodies, anti caspase 3 antibodies and β-catenin antibodies.

The tumors generated by the different clones were sectioned and histologically examined. Cell proliferation levels in the tumor sections were evaluated by immunostaining with anti Proliferating Cell Nuclear Antigen (PCNA) antibodies. A high nuclear staining level was demonstrated in wt hPar1+ Etk/Bmx tumors (p<0.0001, FIG. 12C) as compared with the small tumors produced by hPar1-7A mutant+ Etk/Bmx showing low level of staining (FIG. 12D). Apparently, while an extensive proliferation rate occurs in the wt hPar1 tumor sections, cell proliferation is dramatically attenuated in the hPar1 7A mutant +Etk/Bmx tumors. In-contrast, immunostaining performed by applying anti caspase 3 antibodies showed markedly enhanced cytoplasmic staining in the small appearing tumors generated by the hPar1-7A mutant+Etk/Bmx (p<0.0003, FIG. 12D). Caspases are well known for their central part in apoptosis. Without wishing to be bound by theory, it seems that apoptosis may be actively on-going in the small appearing tumors generated by hPar1 7A mutant. In-contrast, no apoptosis was observed in the wt hPar1 generated tumors. When the levels of β-catenin were evaluated, distinctly high nuclear localization of β-catenin was observed in the wt hPar1+ Etk/Bmx tumors. In-contrast, weak cytoplasmic staining was seen in hPar1-7A mutant+Etk/Bmx small tumors (FIG. 12D). These data reaffirm that wt hPar1 in the presence of Etk/Bmx generated large tumors while hPar1-7A mutant+Etk/Bmx were incapable of producing growing tumors. Rather, the mutant hPar1-7A+Etk/Bmx showed a reduced proliferation rate, enhanced apoptotic levels and low levels of β-catenin (an indicator of oncogenicity) localized in the cytoplasmic fraction of the cells. The identification of a $PAR_1$ C-tail binding domain provides a platform for new therapeutic vehicles in the treatment of cancer, and in particular breast cancer.

Example 3

The $PAR_2$ C-Tail Minimal Binding Site for Etk/Bmx

Figure 13:
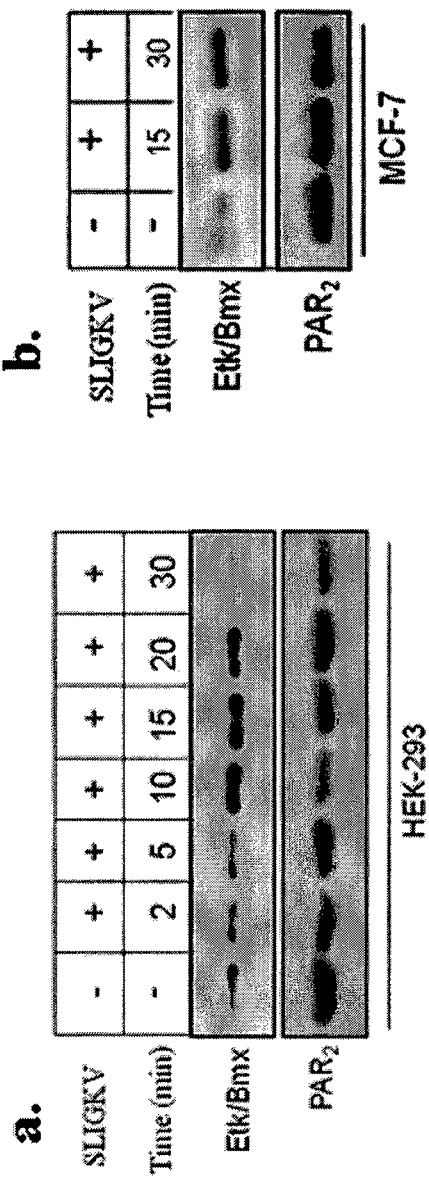
FIG. 13A is a gel showing co-immunoprecipitation analyses using anti PAR2 antibodies and anti Etk/Bmx antibodies.
FIG. 13B is a gel showing GST-PAR2 C-tails: wt and deleted tails.

HEK-293T cells were transiently transfected with both hPar2 and T7-tagged Etk/Bmx. Immunoprecipitation analyses were performed before and after $PAR_2$ activation with SLIGKV (a peptide known to activate $PAR_2$). The results showed a firm association between $PAR_2$ and Etk/Bmx, occurring between 10-20 min of activation which declined immediately thereafter (FIG. 13a). Similar outcome was obtained in MCF7 cells transfected to express both hPar2 as well as Etk/Bmx (FIG. 13b). These data clearly indicate that $PAR_2$ behaves in a similar manner as $PAR_1$ following activation and associates with Etk/Bmx.

Figure 14:
FIG. 14A is a gel showing the binding between Etk/Bmx expressing cell lysates and GST-PAR2 C-tails.
FIG. 14B is a gel showing the binding between Etk/Bmx expressing cell lysates and various truncated GST-PAR2 C-tails. Lanes: A. control, B. GST-PAR2C-tail wt; C. GST-PAR2C-tail K378Z; D. GST-PAR2C-tail K3356Z.

The physical association between Etk/Bmx and $PAR_2$ was confirmed in assay examining the binding between Etk/Bmx expressing cell lysates and GST-$PAR_2$ C-tails. A truncated form of hPar2 showed no physical interaction between $PAR_2$ and Etk/Bmx as compared with wt hPar2 (FIG. 14A). Various $PAR_2$ deletion constructs were used to identify the minimal binding domain within $PAR_2$ C-tail as shown in FIG. 14B. Lanes: A. control, B. GST-PAR2C-tail wt; C. GST-$PAR_2$C-tail K378Z; D. GST-$PAR_2$C-tail K3356Z. Apparently, the smallest c-tail analyzed, K365Z, exhibits effective association. The minimal signal binding region in the $PAR_2$ C-tail was found to be: NH2-SHDFRDHA-COOH.

Example 4

Inhibition of $PAR_2$ Signaling In Vivo

The physiological significance of a prime signaling partner that interacts with $PAR_2$ C-tail is assessed in vivo, in an orthotopic mammary fat pad model for tumor development. As shown above in example 2, stable MCF7 clones expressing various constructs of hPar2 are generated and injected orthotopically into mice, mammary glands. These clones include wt hPar2, truncated hPar2 (devoid of the cytoplasmic tail) and the various deleted hPar2-C-tail constructs (e.g., K390Z hPar2; K378Z hPar2, K368Z hPar2 and K356Z hPar2). In parallel, a silenced siRNA-hPar2 lentiviral construct is evaluated for the ability to halt tumor growth, in vivo. For the cloning of siRNA-hPar2 into a lentiviral vector the following primers are used

P-TG GGAAGAAGCCTTATTGGTA TTCAAGAGA-TACCAATAA GGC TTCTTCCCTTTTTC (SEQ ID NO: 53)

5'-P-TCGAGAAAAAAG GGAA GAAGCC TTATTGG-TATC TCTTGAATACCAATA AGGCTTCTTCCCA (SEQ ID NO: 54). Stable clones expressing both wt hPar2 and the mutated hPar2 C-tail (incapable of binding a prime signaling partner; e.g. Etk/Bmx) are generated. These clones are analyzed in vivo to evaluate the physiological significance for preventing a prime signaling partner association with $PAR_2$.

Example 5

Figure 15:
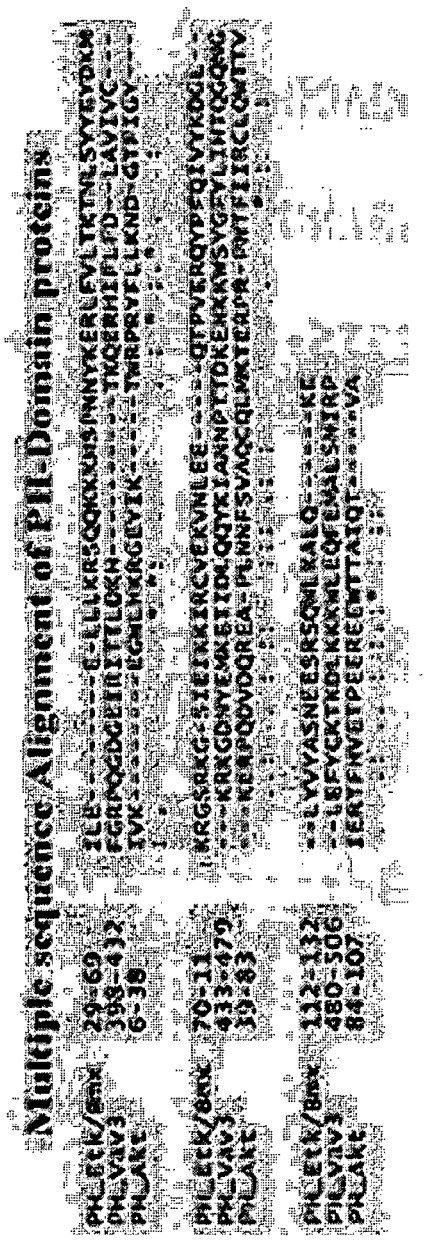
FIG. 15 is a schematic representation showing the sequence alignment of the PH domain of the proteins Etk/Bmx (SEQ ID NO: 61), vav3 (SEQ ID NO: 62) and Akt (SEQ ID NO: 63).

Selective Association of Additional PH-Domain Containing Signal Proteins with $PAR_1$ and $PAR_2$ The association between Etk/Bmx and $PAR_1$-C-tail occurs via Etk/Bmx's PH-domain. Next, the association of additional PH-domain containing proteins, e.g. Akt and Vav3 with $PAR_1$ or $PAR_2$ was examined. FIG. 15 shows the sequence alignment of the PH domain of the proteins Etk/Bmx, vav3 and Akt.

Figure 16:
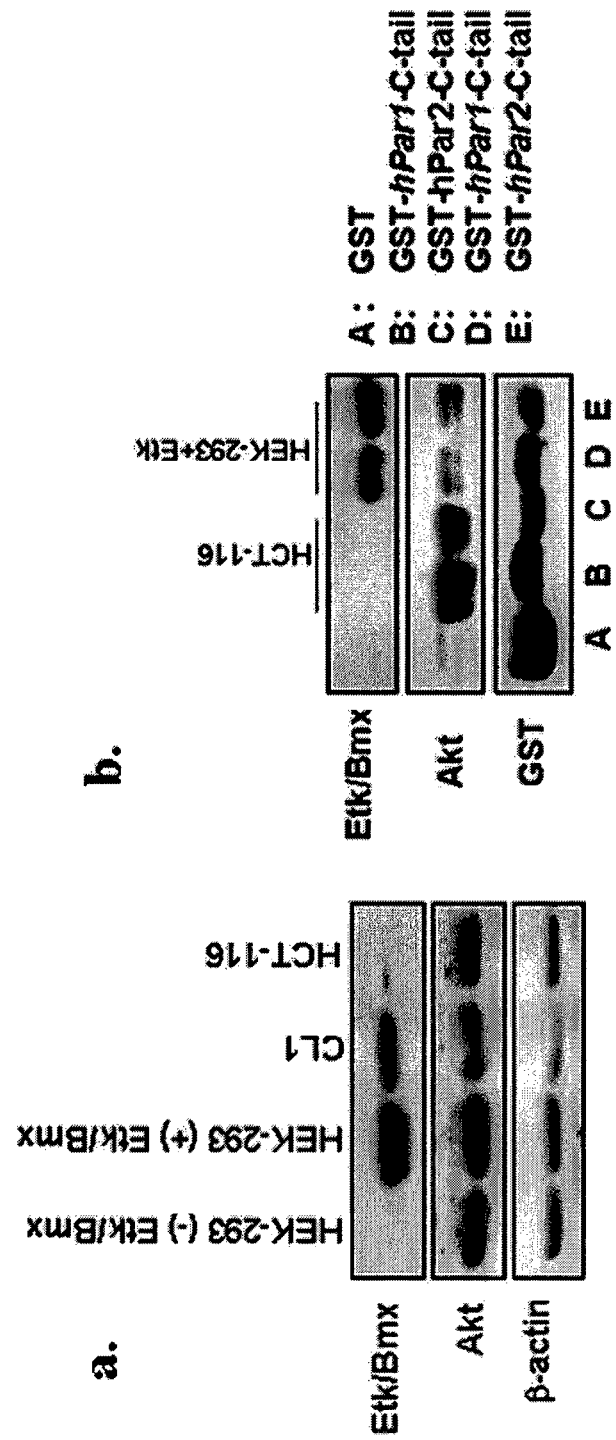
FIG. 16A is a gel showing expression of Akt and Etk/Bmx in various cell lines (CL1, HEK-293 and HCT-116).
FIG. 16B is a gel showing binding immobilization of cell lysates following application on GST beads of either $PAR_1$-C-tail or $PAR_2$-C-tail. Lane A: GST column alone: Lanes B, C: HCT-116; Lanes D, E: HEK-293T+Etk.

First, the endogenous level of Akt and Etk/Bmx was analyzed in various tumor cell lines (i.e. HEK-293T, CL1, HCT116, MDA-MB-231, and MDA-MB-435). While Akt is abundantly expressed in all lines tested, Etk/Bmx appeared endogenously only in CL1, a prostate cancer cell line (FIG. 16A). Next, binding immobilization of cell lysates following application on GST beads of either $PAR_1$-C-tail or $PAR_2$-C-tail was employed. While no binding was observed on a GST column alone, specific binding was seen in HEK-293T cells that were ectopically transfected to express Etk/Bmx. This binding was found in both GST-$PAR_1$-C-tail and also in GST-$PAR_2$-C-tail. However, in HCT-116 cells lacking Etk/Bmx no such binding was seen but rather both $PAR_1$ and $PAR_2$ C-tails effectively associated with Akt (FIG. 16B). Without wishing to be bound by theory, these observations suggest that both $PAR_1$ and $PAR_2$ C-tails bind primarily to Etk/Bmx, but in instances where Etk/Bmx is absent, Akt is potently associated with both PARs C-tails.

Figure 17:
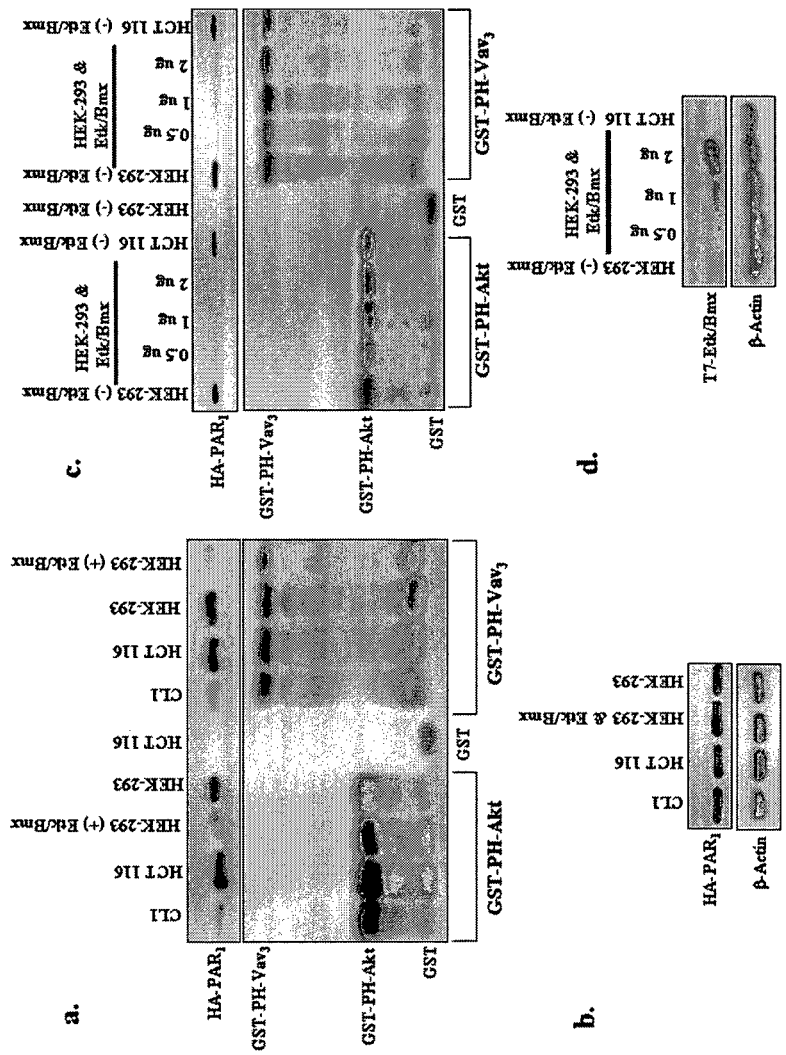
FIG. 17A is a gel showing association of cell lysates of various cell lines (containing HA-PAR1) with GST PH-Akt or GST-PH-Vav$_3$.
FIG. 17B is a gel showing the levels of expression of HA-PAR1 in the various cell lines.
FIG. 17C is a gel showing association of HA-PAR1 with GST PH-Akt or GST-PH-Vav$_3$ in HEK-293T cells transfected with increasing concentrations of Etk/Bmx.
FIG. 17D is a gel showing expression levels of Etk/Bmx in Hek-293T cells transfected with Etk/Bmx.

Next, a panel of cell-lines was transfected with HA-tag-hPar1. Cell lysates were prepared and applied onto GST-PH-Akt or GST-PH-Vav3. HEK-293T cells were used as naïve parental cells (e.g., lacking Etk/Bmx) as also following enforced expression of Etk/Bmx. As shown in FIG. 17A cells that do not express endogenously Etk/Bmx, are capable of effectively associating with PH-Akt (e.g., HCT-116 and HEK-293T cells). In-contrast, cells that express Etk/Bmx either endogenously (e.g., CL1) or following transfection (e.g., HEK-293T cells) fail to physically associate with $PAR_1$. Similarly the same pattern of association was observed when the cell lysates were applied onto GST-PH-$Vav_3$ (FIG. 17A). In order to substantiate the observation that Etk/Bmx preferentially associates with $PAR_1$-C-tail, increasing concentrations of Etk/Bmx were transfected into HEK-293T cells. Indeed, while naïve HEK-293T cells displayed potent binding with the PH-domain of either. Akt or $Vav_3$, the presence of Etk/Bmx abrogated these associations, at the lowest concentration used for transfection (e.g., 0.5 μg) (FIG. 17C). This outcome supports the hypothesis that Etk/Bmx associates preferentially with $PAR_1$-C-tail, however that it is capable of associating with other PH-domain containing signal proteins.

The PH-Domain Binding Region in $PAR_1$-C-Tail

Figure 18:
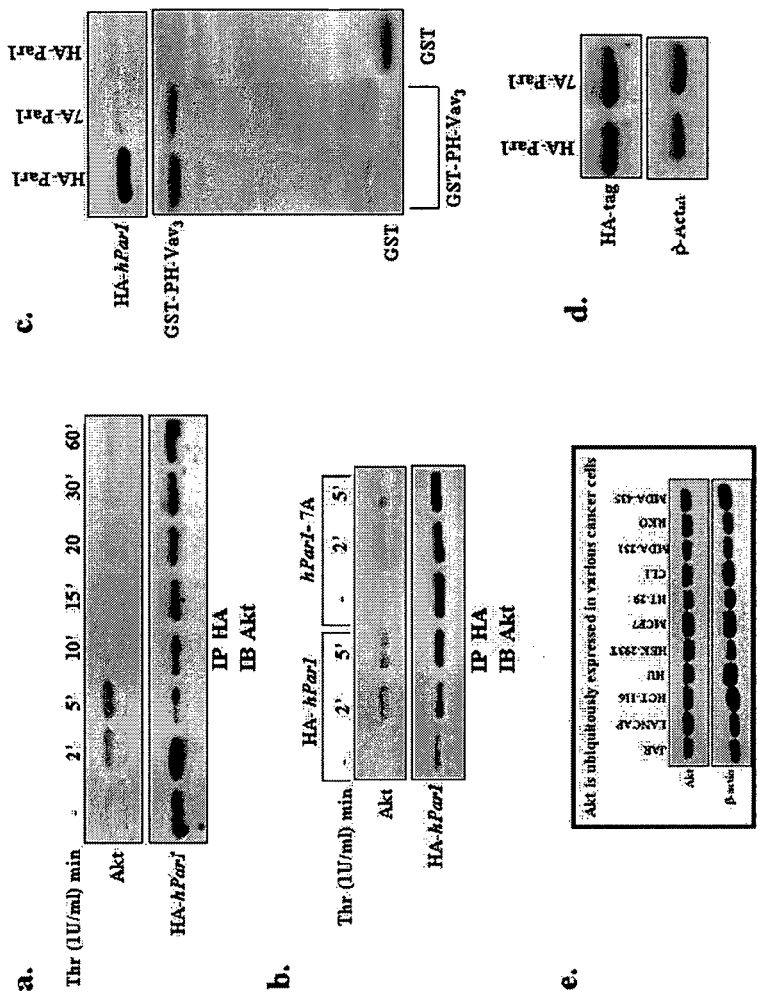
FIG. 18A is a gel showing levels of co-immunoprecipitation between Akt and PAR1 at various time points following activation.
FIG. 18B is a gel showing levels of co-immunoprecipitation between Akt and PAR$_1$ at various time points following activation in cells transfected with either wt hPar1 or with the mutant hPar1-7 A, incapable of binding Etk/Bmx.
FIG. 18C is a gel showing association between cell lysates expressing either wt hPar1 or the mutant hPar1 7A and GST-PH-Vav$_3$.
FIG. 18D is a gel showing expression of HA-tag in cells transfected with ha-PAR1 and in cells transfected with the mutant PAR1-7A.
FIG. 18E is a gel showing expression of Akt in various cancer cells.

The following example demonstrates that the association of $PAR_1$-C-tail with PH-domain containing proteins, e.g. PH-domain-Akt or PH-domain-$Vav_3$ occurs via the same region that is associated with Etk/Bmx. Namely, without wishing to be bound by theory the $PAR_1$-C-tail appears to be an anchor region for association with PH-domain containing proteins. For this purpose, the association between Akt (which is ubiquitously expressed in the cells) and $PAR_1$ was analyzed, following activation. As shown in FIG. 18, Co-immunoprecipitation between Akt and $PAR_1$ was obtained following 2 and 5 minutes activation, and declined immediately thereafter. Nearly normal epithelial HU cells were next transfected with either wt hPar1 or with the mutant hPar1-7A, incapable of binding Etk/Bmx. Immunoprecipitation analyses showed that while potent association between Akt and $PAR_1$ was observed in the presence of wt hPar1, no association was seen when the mutant hPar1 7A was present (FIGS. 18 A and B). Likewise, when cell lysates expressing either wt hPar1 or the mutant hPar1 7A, were applied on GST-PH-$Vav_3$ an essentially similar pattern of association occurred. While the wt form firmly binds to $PAR_1$-C-tail, it completely failed to bind in the presence of the mutant $PAR_1$-7A (FIG. 18C).

The PH-Domain Binding Region in $PAR_2$-C-Tail

Figure 19:
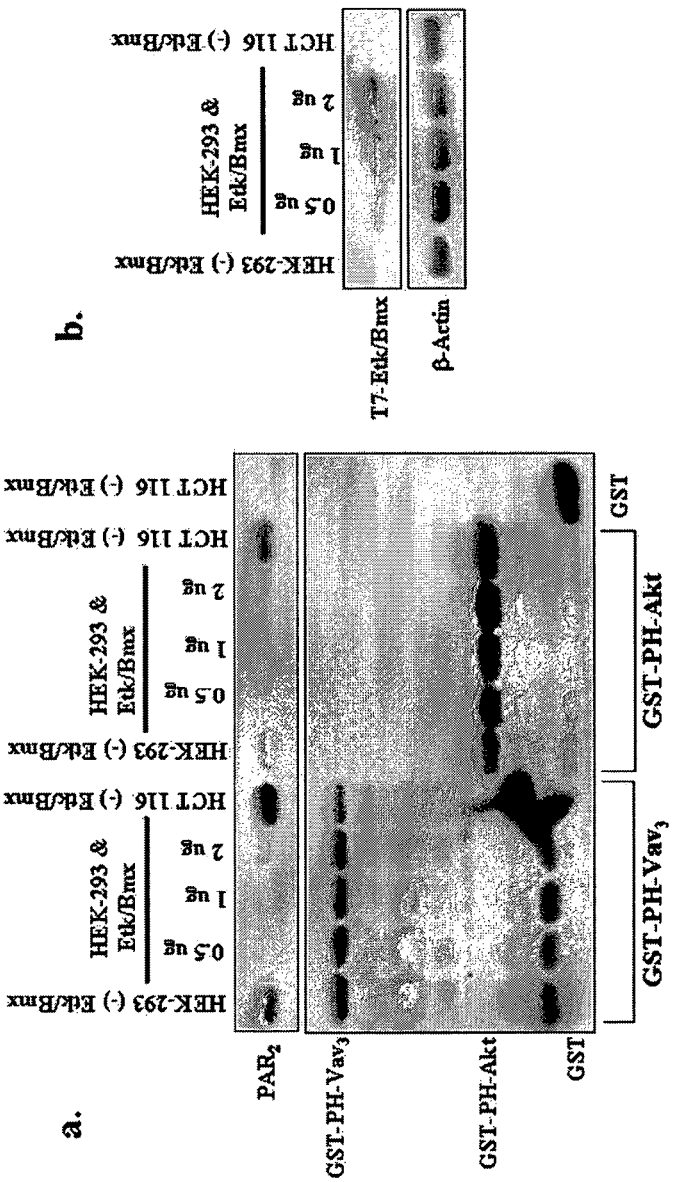
FIG. 19A is a gel showing association between PAR2 and PH-Akt or PH-Vav$_3$ as demonstrated upon application of various cell lysates on GST immobilized PH-domain columns in the presence of absence of increased concentrations of Etk/Bmx.
FIG. 19B is a gel showing expression levels of Etk/Bmx.

Cells that do not express endogenous Etk/Bmx effectively associated with either PH-Akt or PH-$Vav_3$ as demonstrated upon application on GST immobilized PH-domain columns. HEK-293 cells effectively bind PH-Akt or PH-$Vav_3$. In-contrast, when these cells were transfected with increased concentrations of Etk/Bmx (e.g., 0.5-2 μg) they completely failed to associate with either of the PH-domain proteins analyzed (e.g., Akt and $Vav_3$). These data strongly indicate that activation of $PAR_2$ behaves in a similar manner as activated $PAR_1$ and primarily associates with the PH-domain of Etk/Bmx (FIG. 19). Once Etk/Bmx is absent, other signal containing PH-domain/s can associate with $PAR_2$-C-tail as portrayed via binding to both Akt and $Vav_3$.

Figure 20:
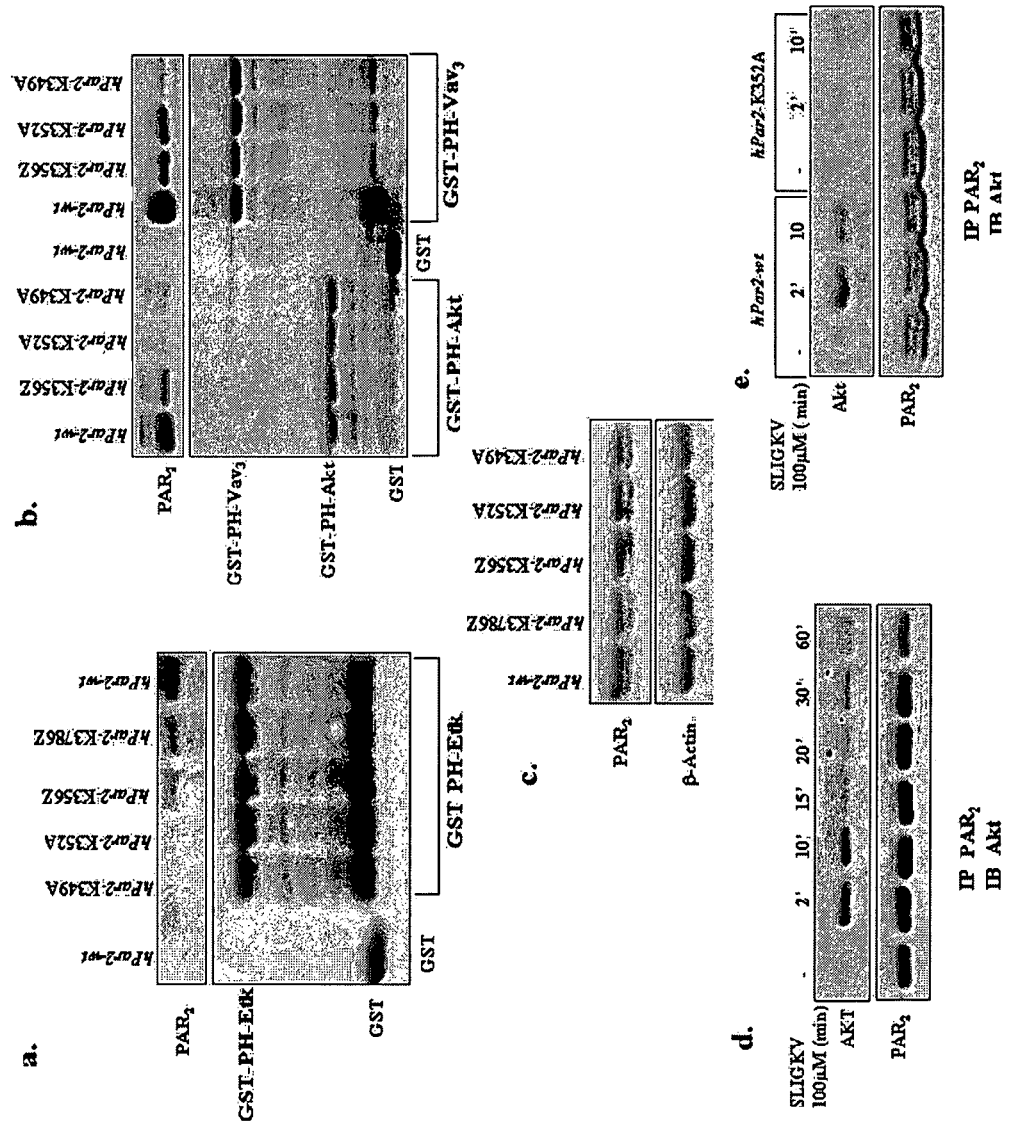
FIGS. 20A and 20B are gels showing levels of binding between mutant versions of PAR2 c-tail (e.g., K352A, K349A, K356Z) and PH-Etk/Bmx (20A) or PH-Vav$_3$ or PH-Akt (20B).
FIG. 20C shows PAR$_2$ expression levels.
FIG. 20D shows immunoprecipitation analyses before and after PAR$_2$ SLIGKV activation of PAR$_2$ and Akt at 2 and 10 minutes following activation.
FIG. 20E is a gel showing the association between PAR2 and Akt in wild type PAR2 compared with the mutant form K352A.

In order to determine the minimal binding region within $PAR_2$-C-tail sequence, deleted hPar2-C-tail constructs were prepared. HEK-293T cells were transfected to overexpress either wt hPar2 or the shortest hPar2 deleted construct (e.g., hPar2 K356Z) or mutants inserted into the shortest Etk/Bmx, Akt or $Vav_3$. Slightly weaker binding is observed in the presence of the shortest region K356A. When mutants were applied to this region (e.g., K352A, K349A) both mutants failed to bind either Etk/Bmx (FIG. 20A) or Akt. While the mutant K352A still showed weak binding to $Vav_3$-PH-domain, the mutant K349A exhibited complete abrogation of this binding (FIG. 20B). Immunoprecipitation analyses before and after $PAR_2$ SLIGKV activation showed association (as evidenced by co-immunoprecipitation) between $PAR_2$ and Akt at 2 and 10 minutes following activation (FIG. 20D). Indeed, when the mutant K352A was present it abrogated the association between $PAR_2$ and Akt (FIG. 20E). Altogether, these observations collectively show that the binding association to the different PH proteins is largely mediated through the same region within $PAR_2$-C-tail.

Example 6

$PAR_1$ Peptide Penetration into MCF7 Cells

Figure 21:
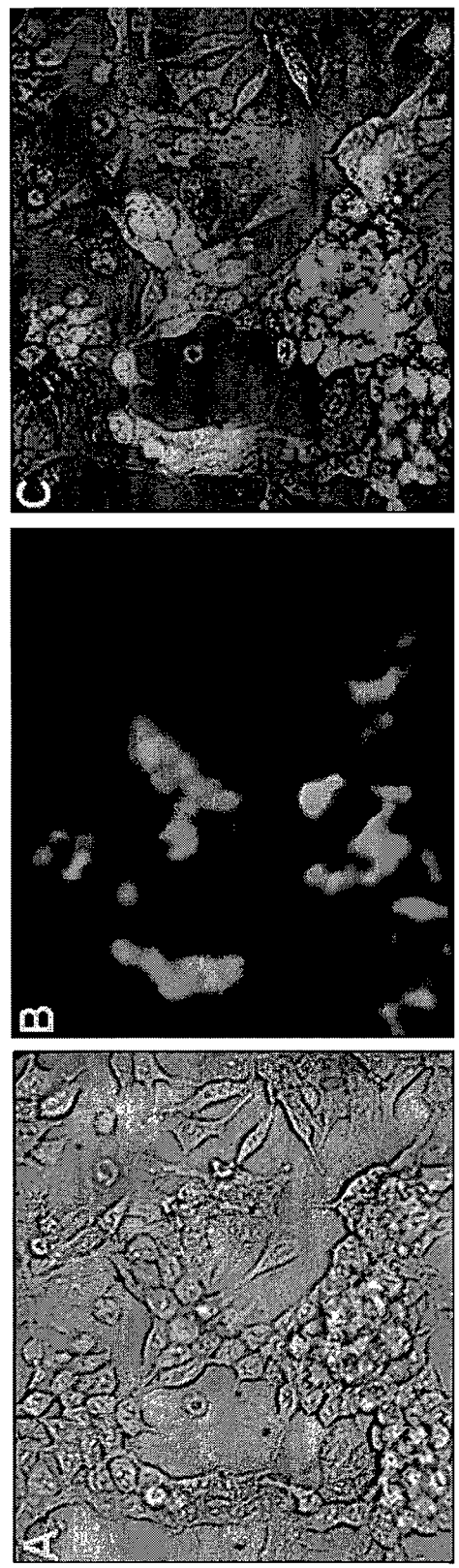
FIG. 21A is a photograph showing MCF7 cells.
FIGS. 21B and 21C show GFP-stained MCF7 cells.

A $PAR_1$ peptide corresponding to the region which associates with the PH-domain (i.e. FITC-SSECQRYVYSIL-COOH (SEQ ID NO: 3) was synthesized and tagged with GFP (green fluorescence protein). MCF7 cells were preincubated for various time periods with the FITC-labeled peptide (e.g., 2 h, 4 h, 8 h and 16 h). After 2 h, some of the cells showed uptake of GFP. Maximal uptake was visualized after 8 h and 16 h. The levels of the penetration of the GFP-PH-domain $PAR_1$ peptide into MCF7 cells are shown in FIG. 21. As can be seen in FIGS. 21B and C a large number of GFP containing cells can be observed, indicating that the peptide is capable of penetrating into the cells.

Figure 22:
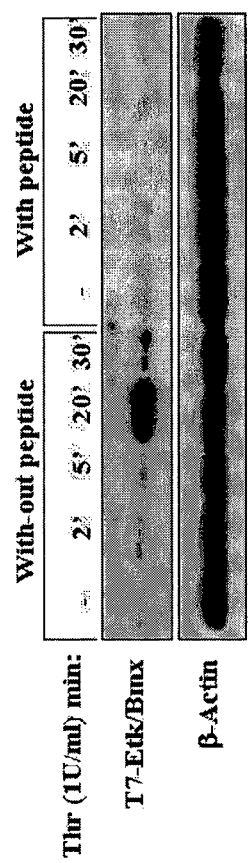
FIG. 22 is a gel demonstrating the association between Etk/Bmx and PAR1-C-tail in the presence and absence of the GFP-labeled peptide.

Next, a competition experiment was performed. Stable clones of MCF7 cells expressing either HA-$PAR_1$ T7-tagged Etk/Bmx, and incubated in the presence or absence of the $PAR_1$ PH-domain peptide (i.e. SSECQRYVYSIL). The cells were activated either by thrombin or using the $PAR_1$ activating peptide TFLLRN, and cell lyzates were prepared at various time points after activation. Immuno-precipitation analyses were performed with anti HA antibodies (thereby immunoprecipitating HA-FARO, followed by Western blot analysis using anti T7 antibodies (detecting T7-tagged Etk/Bmx). As demonstrated in FIG. 22 the association between Etk/Bmx and $PAR_1$-C-tail can be seen following 20 minutes activation without the peptide. No binding is observed in the presence of the peptide under similar conditions. Thus the peptide is capable of preventing effectively the PAR1 signalling cascade.

The invention claimed is:

1. A method of inhibiting protease-activated receptor 2 (PAR2) mediated signal transduction comprising administering a peptide of 8 to 25 amino acids in length comprising the amino acid sequence SHDFRDHA (SEQ ID NO: 2) that is capable of selectively inhibiting the binding of PAR2 and a PH-domain containing protein.

2. A method of treating cancer comprising administering a therapeutically effective amount of a peptide of 8 to 25 amino acids in length comprising the amino acid sequence SHDFRDHA (SEQ ID NO: 2) that is capable of selectively inhibiting the binding of protease-activated receptor 2 (PAR2) and a PH-domain containing protein, or a pharmaceutical composition comprising said peptide to a patient in need thereof.

3. A method according to claim 2 further comprising administering an additional therapeutic agent.

* * * * *

SEQUENCE LISTING

```
<160> NUMBER OF SEQ ID NOS: 63

<210> SEQ ID NO 1
<211> LENGTH: 7
<212> TYPE: PRT
<213> ORGANISM: Homo sapiens

<400> SEQUENCE: 1
```

Cys Gln Arg Tyr Val Tyr Ser
1               5

<210> SEQ ID NO 2
<211> LENGTH: 8
<212> TYPE: PRT
<213> ORGANISM: Homo sapiens

<400> SEQUENCE: 2

Ser His Asp Phe Arg Asp His Ala
1               5

<210> SEQ ID NO 3
<211> LENGTH: 12
<212> TYPE: PRT
<213> ORGANISM: Homo sapiens

<400> SEQUENCE: 3

Ser Ser Glu Cys Gln Arg Tyr Val Tyr Ser Ile Leu
1               5                   10

<210> SEQ ID NO 4
<211> LENGTH: 15
<212> TYPE: PRT
<213> ORGANISM: Homo sapiens

<400> SEQUENCE: 4

Ser Ser Glu Cys Gln Arg Tyr Val Tyr Ser Ile Leu Cys Cys Lys
1               5                   10                  15

<210> SEQ ID NO 5
<211> LENGTH: 15
<212> TYPE: PRT
<213> ORGANISM: Homo sapiens

<400> SEQUENCE: 5

Ser Ser Glu Cys Gln Arg Tyr Val Tyr Ser Ile Leu Cys Cys Ala
1               5                   10                  15

<210> SEQ ID NO 6
<211> LENGTH: 15
<212> TYPE: PRT
<213> ORGANISM: Homo sapiens

<400> SEQUENCE: 6

Ser Ser Glu Cys Gln Arg Tyr Val Tyr Ser Ile Leu Cys Ala Lys
1               5                   10                  15

<210> SEQ ID NO 7
<211> LENGTH: 15
<212> TYPE: PRT
<213> ORGANISM: Homo sapiens

<400> SEQUENCE: 7

Ser Ser Glu Cys Gln Arg Tyr Val Tyr Ser Ile Leu Ala Cys Lys
1               5                   10                  15

<210> SEQ ID NO 8
<211> LENGTH: 15
<212> TYPE: PRT
<213> ORGANISM: Homo sapiens

<400> SEQUENCE: 8

Ser Ser Glu Cys Gln Arg Tyr Val Tyr Ser Ile Ala Cys Cys Lys

```
<210> SEQ ID NO 9
<211> LENGTH: 15
<212> TYPE: PRT
<213> ORGANISM: Homo sapiens

<400> SEQUENCE: 9

Ser Ser Glu Cys Gln Arg Tyr Val Tyr Ser Ala Leu Cys Cys Lys
1               5                   10                  15

<210> SEQ ID NO 10
<211> LENGTH: 15
<212> TYPE: PRT
<213> ORGANISM: Homo sapiens

<400> SEQUENCE: 10

Ser Ser Glu Cys Gln Arg Tyr Val Tyr Ala Ile Leu Cys Cys Lys
1               5                   10                  15

<210> SEQ ID NO 11
<211> LENGTH: 15
<212> TYPE: PRT
<213> ORGANISM: Homo sapiens

<400> SEQUENCE: 11

Ser Ser Glu Cys Gln Arg Tyr Val Ala Ser Ile Leu Cys Cys Lys
1               5                   10                  15

<210> SEQ ID NO 12
<211> LENGTH: 15
<212> TYPE: PRT
<213> ORGANISM: Homo sapiens

<400> SEQUENCE: 12

Ser Ser Glu Cys Gln Arg Tyr Ala Tyr Ser Ile Leu Cys Cys Lys
1               5                   10                  15

<210> SEQ ID NO 13
<211> LENGTH: 15
<212> TYPE: PRT
<213> ORGANISM: Homo sapiens

<400> SEQUENCE: 13

Ser Ser Glu Cys Gln Arg Ala Val Tyr Ser Ile Leu Cys Cys Lys
1               5                   10                  15

<210> SEQ ID NO 14
<211> LENGTH: 15
<212> TYPE: PRT
<213> ORGANISM: Homo sapiens

<400> SEQUENCE: 14

Ser Ser Glu Cys Gln Ala Tyr Val Tyr Ser Ile Leu Cys Cys Lys
1               5                   10                  15

<210> SEQ ID NO 15
<211> LENGTH: 15
<212> TYPE: PRT
<213> ORGANISM: Homo sapiens

<400> SEQUENCE: 15

Ser Ser Glu Cys Ala Arg Tyr Val Tyr Ser Ile Leu Cys Cys Lys
1               5                   10                  15
```

<210> SEQ ID NO 16
<211> LENGTH: 15
<212> TYPE: PRT
<213> ORGANISM: Homo sapiens

<400> SEQUENCE: 16

Ser Ser Glu Ala Gln Arg Tyr Val Tyr Ser Ile Leu Cys Cys Lys
1               5                   10                  15

<210> SEQ ID NO 17
<211> LENGTH: 15
<212> TYPE: PRT
<213> ORGANISM: Homo sapiens

<400> SEQUENCE: 17

Ser Ser Ala Cys Gln Arg Tyr Val Tyr Ser Ile Leu Cys Cys Lys
1               5                   10                  15

<210> SEQ ID NO 18
<211> LENGTH: 15
<212> TYPE: PRT
<213> ORGANISM: Homo sapiens

<400> SEQUENCE: 18

Ser Ala Glu Cys Gln Arg Tyr Val Tyr Ser Ile Leu Cys Cys Lys
1               5                   10                  15

<210> SEQ ID NO 19
<211> LENGTH: 15
<212> TYPE: PRT
<213> ORGANISM: Homo sapiens

<400> SEQUENCE: 19

Ala Ser Glu Cys Gln Arg Tyr Val Tyr Ser Ile Leu Cys Cys Lys
1               5                   10                  15

<210> SEQ ID NO 20
<211> LENGTH: 9
<212> TYPE: PRT
<213> ORGANISM: Homo sapiens

<400> SEQUENCE: 20

Ser His Asp Phe Arg Asp His Ala Glx
1               5

<210> SEQ ID NO 21
<211> LENGTH: 9
<212> TYPE: PRT
<213> ORGANISM: Homo sapiens

<400> SEQUENCE: 21

Ser Ala Ala Ala Arg Asp His Ala Glx
1               5

<210> SEQ ID NO 22
<211> LENGTH: 9
<212> TYPE: PRT
<213> ORGANISM: Homo sapiens

<400> SEQUENCE: 22

Ser His Asp Phe Ala Ala Ala Ala Glx
1               5

<210> SEQ ID NO 23

<211> LENGTH: 44
<212> TYPE: DNA
<213> ORGANISM: Artificial Sequence
<220> FEATURE:
<223> OTHER INFORMATION: Primer 1

<400> SEQUENCE: 23
cccctttgtc tattactttg tttcagctgc tgccagggat catg        44

<210> SEQ ID NO 24
<211> LENGTH: 45
<212> TYPE: DNA
<213> ORGANISM: Artificial Sequence
<220> FEATURE:
<223> OTHER INFORMATION: Primer 1

<400> SEQUENCE: 24
gcatgatccc tggcagcagc tgaaacaaag taatagacaa agggg       45

<210> SEQ ID NO 25
<211> LENGTH: 43
<212> TYPE: DNA
<213> ORGANISM: Artificial Sequence
<220> FEATURE:
<223> OTHER INFORMATION: Primer 2

<400> SEQUENCE: 25
cacatgattt cgcggctgct gcaaagaacg ctctcctttg ccg         43

<210> SEQ ID NO 26
<211> LENGTH: 43
<212> TYPE: DNA
<213> ORGANISM: Artificial Sequence
<220> FEATURE:
<223> OTHER INFORMATION: Primer 2

<400> SEQUENCE: 26
cggcaaagga gagcgttctt tgcagcagcc gcgaaatcat gtg         43

<210> SEQ ID NO 27
<211> LENGTH: 23
<212> TYPE: DNA
<213> ORGANISM: Artificial Sequence
<220> FEATURE:
<223> OTHER INFORMATION: Primer GAPDH - sense

<400> SEQUENCE: 27
ccacccatgg caaattccat ggc                               23

<210> SEQ ID NO 28
<211> LENGTH: 24
<212> TYPE: DNA
<213> ORGANISM: Artificial Sequence
<220> FEATURE:
<223> OTHER INFORMATION: Primer GAPDH - antisense

<400> SEQUENCE: 28
tctagacggc aggtcaggtc cacc                              24

<210> SEQ ID NO 29
<211> LENGTH: 20
<212> TYPE: DNA
<213> ORGANISM: Artificial Sequence
<220> FEATURE:
<223> OTHER INFORMATION: Primer hPar1-sense

<400> SEQUENCE: 29
ctcgtcctca aggagcaaac                                               20

<210> SEQ ID NO 30
<211> LENGTH: 20
<212> TYPE: DNA
<213> ORGANISM: Artificial Sequence
<220> FEATURE:
<223> OTHER INFORMATION: Primer hPar1- antisense

<400> SEQUENCE: 30
tgggatcgga actttctttg                                               20

<210> SEQ ID NO 31
<211> LENGTH: 24
<212> TYPE: DNA
<213> ORGANISM: Artificial Sequence
<220> FEATURE:
<223> OTHER INFORMATION: C-tail primer - sense

<400> SEQUENCE: 31
tactattacg ctggatcctc tgag                                          24

<210> SEQ ID NO 32
<211> LENGTH: 24
<212> TYPE: DNA
<213> ORGANISM: Artificial Sequence
<220> FEATURE:
<223> OTHER INFORMATION: C-tail primer - antisense

<400> SEQUENCE: 32
cttgaattcc taagttaaca gctt                                          24

<210> SEQ ID NO 33
<211> LENGTH: 54
<212> TYPE: PRT
<213> ORGANISM: Artificial Sequence
<220> FEATURE:
<223> OTHER INFORMATION: entire PAR1 C-tail site

<400> SEQUENCE: 33

Tyr Tyr Tyr Ala Ser Ser Glu Cys Gln Arg Tyr Val Tyr Ser Ile Leu
 1               5                  10                  15

Cys Cys Lys Glu Ser Ser Asp Pro Ser Tyr Asn Ser Ser Gly Gln Leu
            20                  25                  30

Met Ala Ser Lys Met Asp Thr Cys Ser Ser Asn Leu Asn Asn Ser Ile
        35                  40                  45

Tyr Lys Lys Leu Leu Thr
    50

<210> SEQ ID NO 34
<211> LENGTH: 6
<212> TYPE: PRT
<213> ORGANISM: Homo sapiens

<400> SEQUENCE: 34

Ser Phe Leu Leu Arg Asn
 1               5

<210> SEQ ID NO 35
<211> LENGTH: 10
<212> TYPE: PRT
<213> ORGANISM: Homo sapiens

<400> SEQUENCE: 35

Thr Phe Leu Leu Arg Asn Pro Asn Asp Lys
    1               5                   10

<210> SEQ ID NO 36
<211> LENGTH: 21
<212> TYPE: DNA
<213> ORGANISM: Artificial Sequence
<220> FEATURE:
<223> OTHER INFORMATION: Y397Z primer - sense

<400> SEQUENCE: 36
ataagcattg accggtttct g                                       21

<210> SEQ ID NO 37
<211> LENGTH: 30
<212> TYPE: DNA
<213> ORGANISM: Artificial Sequence
<220> FEATURE:
<223> OTHER INFORMATION: Y397Z primer - antisense

<400> SEQUENCE: 37
gctctagatt ttaactgctg ggatcggaac                              30

<210> SEQ ID NO 38
<211> LENGTH: 30
<212> TYPE: DNA
<213> ORGANISM: Artificial Sequence
<220> FEATURE:
<223> OTHER INFORMATION: Primer 381- sense

<400> SEQUENCE: 38
tgccagaggg ctgtctacag tatcttatgc                              30

<210> SEQ ID NO 39
<211> LENGTH: 30
<212> TYPE: DNA
<213> ORGANISM: Artificial Sequence
<220> FEATURE:
<223> OTHER INFORMATION: Primer 381 - antisense

<400> SEQUENCE: 39
gatactgtag acagccctct ggcactcaga                              30

<210> SEQ ID NO 40
<211> LENGTH: 35
<212> TYPE: DNA
<213> ORGANISM: Artificial Sequence
<220> FEATURE:
<223> OTHER INFORMATION: Primer 383 - sense

<400> SEQUENCE: 40
gccagaggta cgtcgcaagt atcttatgct gcaaa                        35

<210> SEQ ID NO 41
<211> LENGTH: 31
<212> TYPE: DNA
<213> ORGANISM: Artificial Sequence
<220> FEATURE:
<223> OTHER INFORMATION: Primer 383- antisense

<400> SEQUENCE: 41
aagatacttg cgacgtacct ctggcactca g                            31

<210> SEQ ID NO 42
<211> LENGTH: 14

```
<212> TYPE: PRT
<213> ORGANISM: Homo sapiens

<400> SEQUENCE: 42

Ser Ser Glu Cys Gln Arg Tyr Val Tyr Ser Ile Leu Cys Cys
 1               5                  10

<210> SEQ ID NO 43
<211> LENGTH: 14
<212> TYPE: PRT
<213> ORGANISM: Homo sapiens

<400> SEQUENCE: 43

Ser Ser Glu Ala Ala Ala Ala Ala Ala Ile Leu Cys Cys
 1               5                  10

<210> SEQ ID NO 44
<211> LENGTH: 27
<212> TYPE: DNA
<213> ORGANISM: Artificial Sequence
<220> FEATURE:
<223> OTHER INFORMATION: Primer for HA-tag - sense

<400> SEQUENCE: 44
tacccatacg atgttccaga ttacgct                                      27

<210> SEQ ID NO 45
<211> LENGTH: 26
<212> TYPE: DNA
<213> ORGANISM: Artificial Sequence
<220> FEATURE:
<223> OTHER INFORMATION: Primer for HA-tag - antisense

<400> SEQUENCE: 45
agcgtaatct ggaacatcta tgggta                                       26

<210> SEQ ID NO 46
<211> LENGTH: 33
<212> TYPE: DNA
<213> ORGANISM: Artificial Sequence
<220> FEATURE:
<223> OTHER INFORMATION: Primer hPar17A mutant - sense

<400> SEQUENCE: 46
tctgaggctg ctgctgctgc tgcagctatc tta                               33

<210> SEQ ID NO 47
<211> LENGTH: 33
<212> TYPE: DNA
<213> ORGANISM: Artificial Sequence
<220> FEATURE:
<223> OTHER INFORMATION: Primer hPAr17A mutant - antisense

<400> SEQUENCE: 47
taagatagct gcagcagcag cagcagcctc aga                               33

<210> SEQ ID NO 48
<211> LENGTH: 24
<212> TYPE: DNA
<213> ORGANISM: Homo sapiens

<400> SEQUENCE: 48
tactattacg ctggatcctc tgag                                         24

<210> SEQ ID NO 49
```

```
<211> LENGTH: 23
<212> TYPE: DNA
<213> ORGANISM: Homo sapiens

<400> SEQUENCE: 49
ctgaattcct aagttaacag ctt                                          23

<210> SEQ ID NO 50
<211> LENGTH: 16
<212> TYPE: PRT
<213> ORGANISM: Artificial Sequence
<220> FEATURE:
<223> OTHER INFORMATION: Synthetic peptide

<400> SEQUENCE: 50

Cys Leu Leu Arg Asn Pro Asn Asp Lys Tyr Glu Pro Phe Trp Glu Asp
 1               5                  10                  15

<210> SEQ ID NO 51
<211> LENGTH: 15
<212> TYPE: PRT
<213> ORGANISM: Artificial Sequence
<220> FEATURE:
<223> OTHER INFORMATION: Synthetic peptide

<400> SEQUENCE: 51

Lys Ser Ser Pro Leu Gln Lys Gln Leu Pro Ala Phe Ile Ser Cys
 1               5                  10                  15

<210> SEQ ID NO 52
<211> LENGTH: 10
<212> TYPE: PRT
<213> ORGANISM: Homo sapiens

<400> SEQUENCE: 52

Ser Phe Leu Leu Arg Asn Pro Asn Asp Lys
 1               5                  10

<210> SEQ ID NO 53
<211> LENGTH: 57
<212> TYPE: DNA
<213> ORGANISM: Artificial Sequence
<220> FEATURE:
<223> OTHER INFORMATION: Primer for the cloning siRNA-hPar2

<400> SEQUENCE: 53
tgggaagaag ccttattggt attcaagaga taccaataag gcttcttccc tttttc      57

<210> SEQ ID NO 54
<211> LENGTH: 61
<212> TYPE: DNA
<213> ORGANISM: Artificial Sequence
<220> FEATURE:
<223> OTHER INFORMATION: Primer for the cloning of siRNA-hPar2

<400> SEQUENCE: 54
tcgagaaaaa agggaagaag ccttattggt atctcttgaa taccaataag gcttcttccc  60
a                                                                  61

<210> SEQ ID NO 55
<211> LENGTH: 7
<212> TYPE: PRT
<213> ORGANISM: Homo sapiens

<400> SEQUENCE: 55
```

Arg Ser Phe Leu Leu Arg Asn
1               5

<210> SEQ ID NO 56
<211> LENGTH: 50
<212> TYPE: PRT
<213> ORGANISM: Homo sapiens

<400> SEQUENCE: 56

Ser Ser Glu Cys Gln Arg Tyr Val Tyr Ser Ile Leu Cys Cys Lys Glu
1               5                   10                  15

Ser Ser Asp Pro Ser Tyr Asn Ser Ser Gly Gln Leu Met Ala Ser Lys
            20                  25                  30

Met Asp Thr Cys Ser Ser Asn Leu Asn Asn Ser Ile Tyr Lys Lys Leu
        35                  40                  45

Leu Thr
    50

<210> SEQ ID NO 57
<211> LENGTH: 9
<212> TYPE: PRT
<213> ORGANISM: Homo sapiens

<400> SEQUENCE: 57

Glu Cys Gln Arg Tyr Val Tyr Ser Ile
1               5

<210> SEQ ID NO 58
<211> LENGTH: 9
<212> TYPE: PRT
<213> ORGANISM: Homo sapiens

<400> SEQUENCE: 58

Gln Arg Tyr Val Tyr Ser Ile Leu Cys
1               5

<210> SEQ ID NO 59
<211> LENGTH: 9
<212> TYPE: PRT
<213> ORGANISM: Homo sapiens

<400> SEQUENCE: 59

Asp Pro Ser Ser Tyr Asn Ser Ser Gly
1               5

<210> SEQ ID NO 60
<211> LENGTH: 9
<212> TYPE: PRT
<213> ORGANISM: Homo sapiens

<400> SEQUENCE: 60

Asn Asn Ser Ile Tyr Lys Lys Leu Leu
1               5

<210> SEQ ID NO 61
<211> LENGTH: 104
<212> TYPE: PRT
<213> ORGANISM: Homo sapiens

<400> SEQUENCE: 61

Ile Leu Glu Glu Leu Leu Leu Lys Arg Ser Gln Gln Lys Lys Lys Met
1               5                   10                  15

Ser Pro Asn Asn Tyr Lys Glu Arg Leu Phe Val Leu Thr Lys Thr Asn

```
                    20                  25                  30
Leu Ser Tyr Tyr Glu Tyr Asp Lys Met Lys Arg Gly Ser Arg Lys Gly
                35                  40                  45

Ser Ile Glu Ile Lys Lys Ile Arg Cys Val Glu Lys Val Asn Leu Glu
 50                  55                  60

Glu Gln Thr Pro Val Glu Arg Gln Tyr Pro Phe Gln Ile Val Tyr Lys
65                  70                  75                  80

Asp Gly Leu Leu Tyr Val Tyr Ala Ser Asn Glu Glu Ser Arg Ser Gln
                85                  90                  95

Trp Leu Lys Ala Leu Gln Lys Glu
                100

<210> SEQ ID NO 62
<211> LENGTH: 109
<212> TYPE: PRT
<213> ORGANISM: Homo sapiens

<400> SEQUENCE: 62

Phe Gly Arg Pro Gln Gly Asp Gly Glu Ile Arg Ile Thr Thr Leu Asp
 1               5                  10                  15

Lys His Thr Lys Gln Glu Arg His Ile Phe Leu Phe Asp Leu Ala Val
                20                  25                  30

Ile Val Cys Lys Arg Lys Gly Asp Asn Tyr Glu Met Lys Glu Ile Ile
                35                  40                  45

Asp Leu Gln Gln Tyr Lys Ile Ala Asn Asn Pro Thr Thr Asp Lys Glu
 50                  55                  60

Asn Lys Lys Trp Ser Tyr Gly Phe Tyr Leu Ile His Thr Gln Gly Gln
65                  70                  75                  80

Asn Gly Leu Glu Phe Tyr Cys Lys Thr Lys Asp Leu Lys Lys Lys Trp
                85                  90                  95

Leu Glu Gln Phe Glu Met Ala Leu Ser Asn Ile Arg Pro
                100                 105

<210> SEQ ID NO 63
<211> LENGTH: 102
<212> TYPE: PRT
<213> ORGANISM: Homo sapiens

<400> SEQUENCE: 63

Ile Val Lys Glu Gly Trp Leu His Lys Arg Gly Glu Tyr Ile Lys Thr
 1               5                  10                  15

Trp Arg Pro Arg Tyr Phe Leu Leu Lys Asn Asp Gly Thr Phe Ile Gly
                20                  25                  30

Tyr Lys Glu Arg Pro Gln Asp Val Asp Gln Arg Glu Ala Pro Leu Asn
                35                  40                  45

Asn Phe Ser Val Ala Gln Cys Gln Leu Met Lys Thr Glu Arg Pro Arg
 50                  55                  60

Pro Asn Thr Phe Ile Ile Arg Cys Leu Gln Trp Thr Thr Val Ile Glu
65                  70                  75                  80

Arg Thr Phe His Val Glu Thr Pro Glu Glu Arg Glu Glu Trp Thr Thr
                85                  90                  95

Ala Ile Gln Thr Val Ala
                100
```